United States Patent
Boucneau et al.

(10) Patent No.: US 12,248,670 B2
(45) Date of Patent: Mar. 11, 2025

(54) METHOD AND SYSTEM FOR MULTI-RANGE SLIDER USER INTERFACE CONTROL OF MEDICAL IMAGES

(71) Applicant: GE Precision Healthcare LLC, Wauwatosa, WI (US)

(72) Inventors: Tanguy Boucneau, Yvelines (FR); Lorraine Jammes, Yvelines (FR); Louise Lelievre, Yvelines (FR); Lucile Nosjean, Yvelines (FR); Diana Farfan Cabrera, Yvelines (FR); Cedric Vigne, Yvelines (FR); Adeline Digard Bahuon, Yvelines (FR)

(73) Assignee: GE Precision Healthcare LLC, Waukesha, WI (US)

( * ) Notice: Subject to any disclaimer, the term of this patent is extended or adjusted under 35 U.S.C. 154(b) by 248 days.

(21) Appl. No.: 17/816,335

(22) Filed: Jul. 29, 2022

(65) Prior Publication Data
US 2024/0036719 A1   Feb. 1, 2024

(51) Int. Cl.
*G06F 3/04847* (2022.01)
*G06F 3/0482* (2013.01)
*G06F 3/04886* (2022.01)

(52) U.S. Cl.
CPC ........ *G06F 3/04847* (2013.01); *G06F 3/0482* (2013.01); *G06F 3/04886* (2013.01)

(58) Field of Classification Search
CPC . G06F 3/04847; G06F 3/0482; G06F 3/04886
See application file for complete search history.

(56) References Cited

U.S. PATENT DOCUMENTS

| | | |
|---|---|---|
| 5,491,782 A | 2/1996 | King et al. |
| 7,216,116 B1* | 5/2007 | Nilsson ............... G06F 16/2428 |
| 8,560,966 B2 | 10/2013 | Cotterill |
| 2008/0120565 A1* | 5/2008 | Stiso ................... G06F 3/04847 |
| | | 707/999.102 |

(Continued)

OTHER PUBLICATIONS

"Free jQuery range slider Plugins," jQuery Script Website, Available Online at https://www.jqueryscript.net/tags.php?/range%20slider/, Available as Early as Aug. 12, 2014, 16 pages.

(Continued)

*Primary Examiner* — John T Repsher, III
(74) *Attorney, Agent, or Firm* — Amin, Turocy & Watson, LLP

(57) ABSTRACT

Various methods and systems are provided for a user interface of a medical imaging system. In one embodiment, a method may include displaying a slider bar comprising a track having a fixed range of values, a first slider thumb defining a maximum value of a first adjustable range on the track, and a second slider thumb defining a minimum value of a second adjustable range on the track; operating the first slider thumb and the second slider thumb in one of a linked mode and an unlinked mode; and adjusting one or both of the maximum value of the first adjustable range and the minimum value of the second adjustable range in response to receiving a single user input based on whether the first slider thumb and the second slider thumb are operating in the linked mode or the unlinked mode.

20 Claims, 16 Drawing Sheets
(6 of 16 Drawing Sheet(s) Filed in Color)

(56) References Cited

U.S. PATENT DOCUMENTS

2010/0185976 A1* 7/2010 Sadanandan ........ G06F 3/04847
    715/786
2012/0036480 A1* 2/2012 Warner ............... G06F 3/04847
    715/833

OTHER PUBLICATIONS

"jQuery Bootstrap Slider Plugin Examples," jQuery Script Website, Available Online at https://www.jqueryscript.net/demo/Highly-Customizable-Range-Slider-Plugin-For-Bootstrap-Bootstrap-Slider/, Available as Early as Jan. 4, 2016, 1 page.

Jinkins, S., "Let's Make a Multi-Thumb Slider That Calculates The Width Between Thumbs," CSS-TRICKS Website, Available Online at https://css-tricks.com/lets-make-a-multi-thumb-slider-that-calculates-the-width-between-thumbs/, Jun. 23, 2020, 12 pages.

"React Compound Slider—Simple Value Slider," GitHub Website, Available Online at https://sghall.github.io/react-compound-slider/#/slider-demos/horizontal, Available as Early as Oct. 16, 2020, 3 pages.

* cited by examiner

METHOD AND SYSTEM FOR MULTI-RANGE SLIDER USER INTERFACE CONTROL OF MEDICAL IMAGES

FIELD

Embodiments of the subject matter disclosed herein relate to medical imaging, and more particularly, to imaging user interfaces.

BACKGROUND

While processing medical images, a user may define a plurality of ranges for adjusting display and analysis parameters of the medical images via a graphical user interface (GUI) widget. One such widget may include a slider (or slider bar). In some examples, the plurality of ranges may be controlled by the slider. The slider may comprise a finite track, which may be a horizontal or vertical area defining a potential range of values for each of the plurality of ranges. Each of the plurality of ranges may be defined by a minimum value and a maximum value, and thumbs representing a single point on the finite track may graphically define the minimum value and maximum value on the slider. The user may adjust the minimum value of a range of the plurality of ranges by adjusting a first position of a first thumb on the finite track and the maximum value of the range by adjusting a second position of a second thumb on the finite track.

BRIEF DESCRIPTION

This summary introduces concepts that are described in more detail in the detailed description. It should not be used to identify essential features of the claimed subject matter, nor to limit the scope of the claimed subject matter.

In one aspect, a method can include displaying a slider bar comprising a track having a fixed range of values, a first slider thumb defining a maximum value of a first adjustable range on the track, and a second slider thumb defining a minimum value of a second adjustable range on the track; operating the first slider thumb and the second slider thumb in one of a linked mode and an unlinked mode; and adjusting one or both of the maximum value of the first adjustable range and the minimum value of the second adjustable range in response to receiving a single user input based on whether the first slider thumb and the second slider thumb are operating in the linked mode or the unlinked mode. In this way, a user interface may be more easily and accurately controlled with fewer individual manipulations.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1-16, which relate to various embodiments for controlling user interface components for adjusting medical images. In particular, systems and methods are provided for adjusting operational modes of a slider of a user interface. The slider may be any graphical widget that provides an element of interaction with the GUI, such as a button, scroll bar, and the like. The slider will be also referred to herein as a multi-range slider. The slider may have a plurality of adjustable thumbs wherein each thumb represents a single point on the slider track and may be used to select a single point on the track. The thumbs may define minimum and maximum values for ranges corresponding to different medical image analysis outputs. Controlling the slider via the operational modes described herein may increase an ease of use of the user interface and decrease user error.

The multi-range slider may be implemented for image analysis operations and displaying medical image data obtained via a plurality of medical imaging systems. One example operation is an image segmentation operation, wherein the multi-range slider may be used to define thresholds for a plurality of ranges of image signal values that may correspond to different segmentation outputs. The different segmentation outputs may correspond to different visual indicators that distinguish tissue types, healthy tissue from diseased tissue, and the like. The different visual indicators may comprise shading, false coloring, boundary lines, and/or another type of visual distinction that may be output on corresponding areas of an output medical image, such as via an overlay. As one example, the image segmentation operation may be used to quantify and visually indicate different types of lesions in a lung of a patient. Another example operation includes temporally distinguishing contrast agent update in cerebral vessels in patient images.

Typically, a user may define two adjacent ranges of the multi-range slider. The user may manually set an upper limit of a first range of the two adjacent ranges to be equal to a lower limit of a second range of the two adjacent ranges by, for example, performing several computer operations that include changing the upper limit of the first range via a first slider thumb, changing the lower limit of the second range via a second slider, and setting the lower limit of the second range to the upper limit of the first range via the first and/or second slider thumb. However, this sequence is time intensive and prone to user error.

Figure 1:
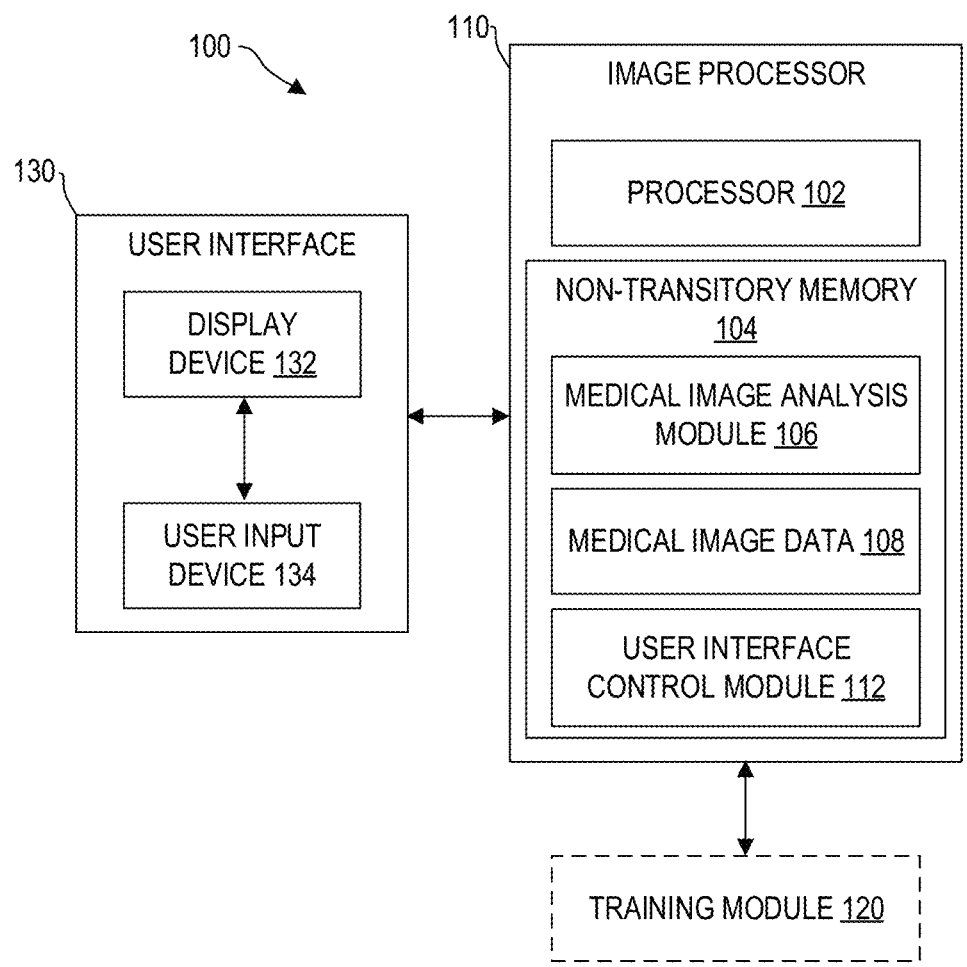
FIG. 1 schematically shows an embodiment of a medical image processing system.
Figure 2:
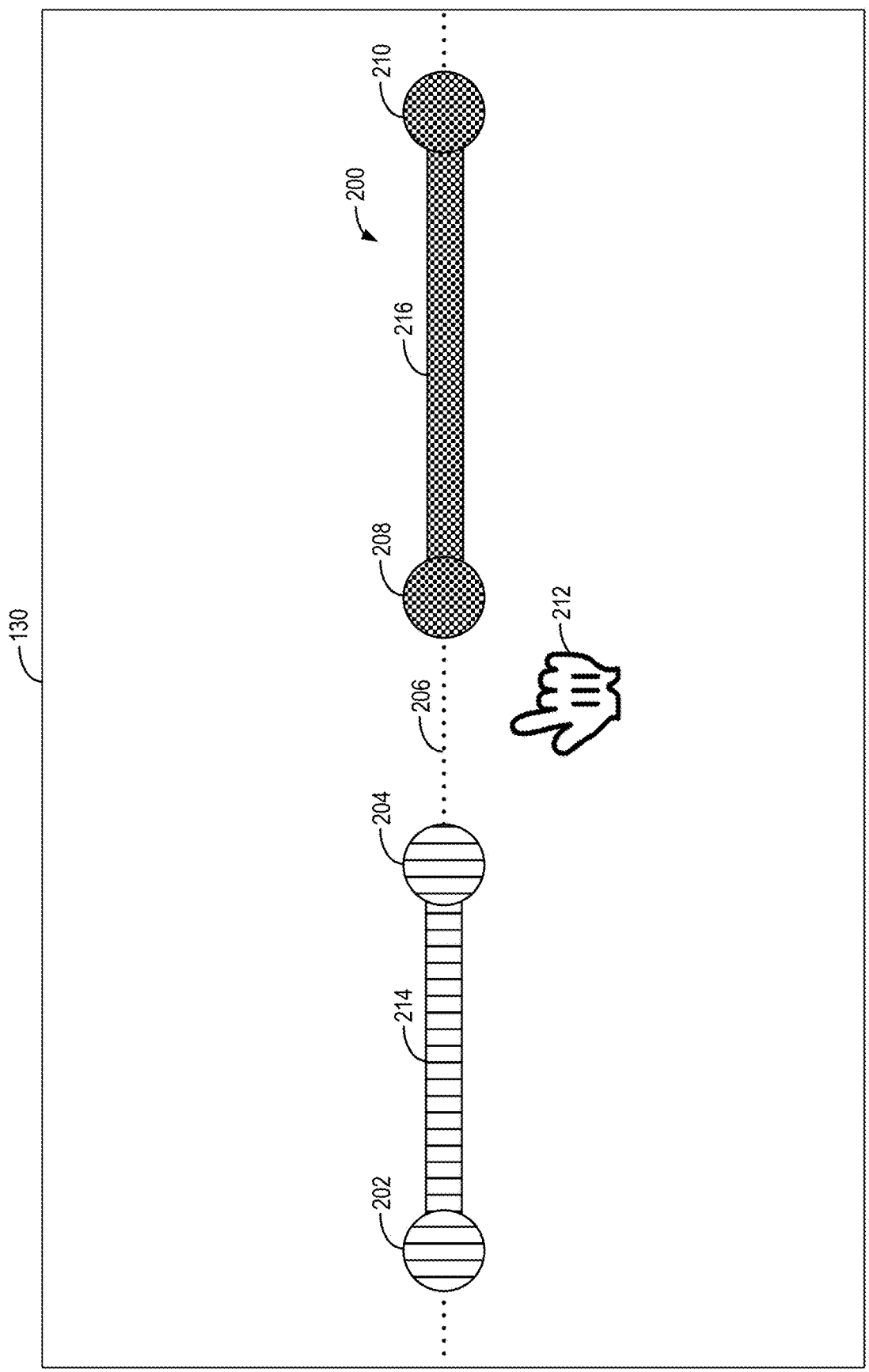
FIG. 2 shows an embodiment of a slider bar including adjustable thumbs on a user interface.
Figure 3:
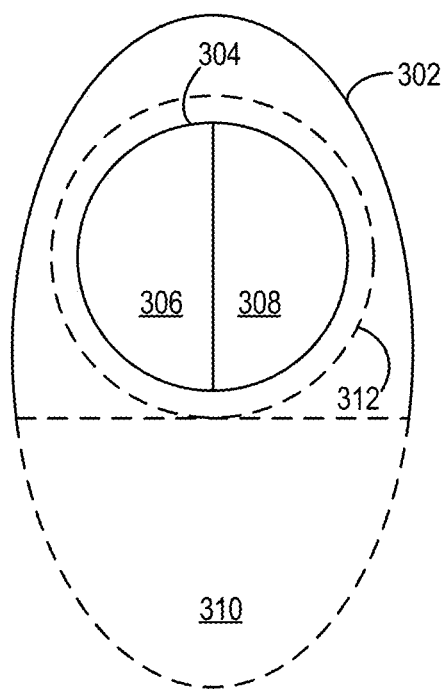
FIG. 3 shows an embodiment of a handle that may be used to operate linked thumbs of a slider bar.

Thus, according to embodiments described herein, a faster and more intuitive slider range control is provided via slider thumb linking and unlinking. An example medical imaging processing system that may be used to evaluate medical imaging data via the user interface control described herein is shown in FIG. 1. An example of a multi-range slider that may be used to adjust an image analysis output via a user interface is shown in FIG. 2. A graphical user interface component of the slider, referred to herein as a handle, may be output by the medical imaging processing system to link the thumbs of adjacent ranges. An example of the handle is shown in FIG. 3. For example, the handle may be output on the user interface when the thumbs of adjacent ranges are linked and may not be output on the user interface when the thumbs of adjacent ranges are unlinked. User input at various touch zones on the handle, also shown in FIG. 3, may enable a specific output, such as thumb movement or unlinking. Thumbs of the multi-range slider in adjacent ranges may be linked to enable dependent movement of thumbs or unlinked to enable independent movement of thumbs according to the methods shown in FIG. 4 and FIG. 5.

Figure 6:
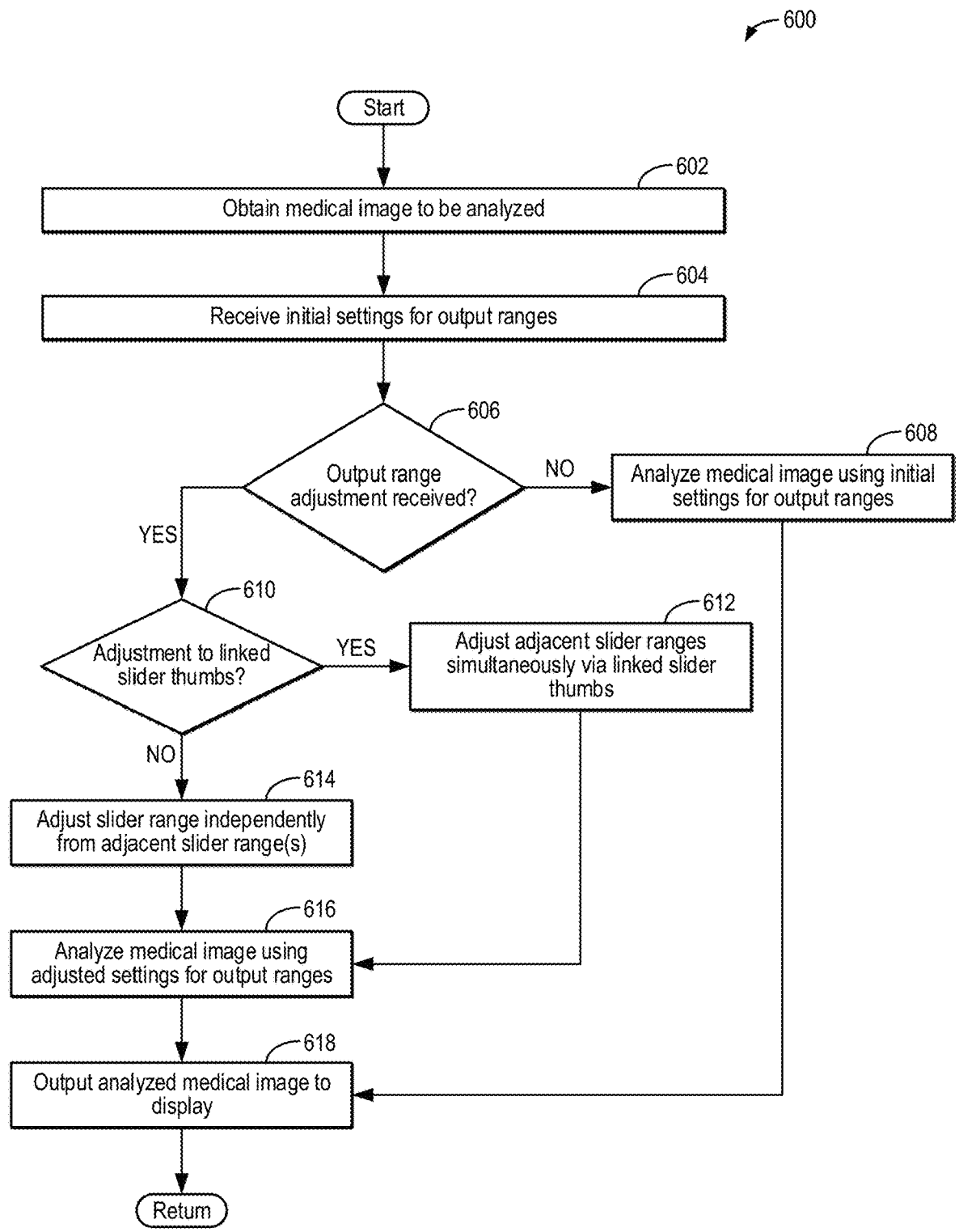
FIG. 6 is a flow chart illustrating an example method for adjusting an analysis output of a medical image via a multi-range slider bar having linkable range control.
Figure 7:
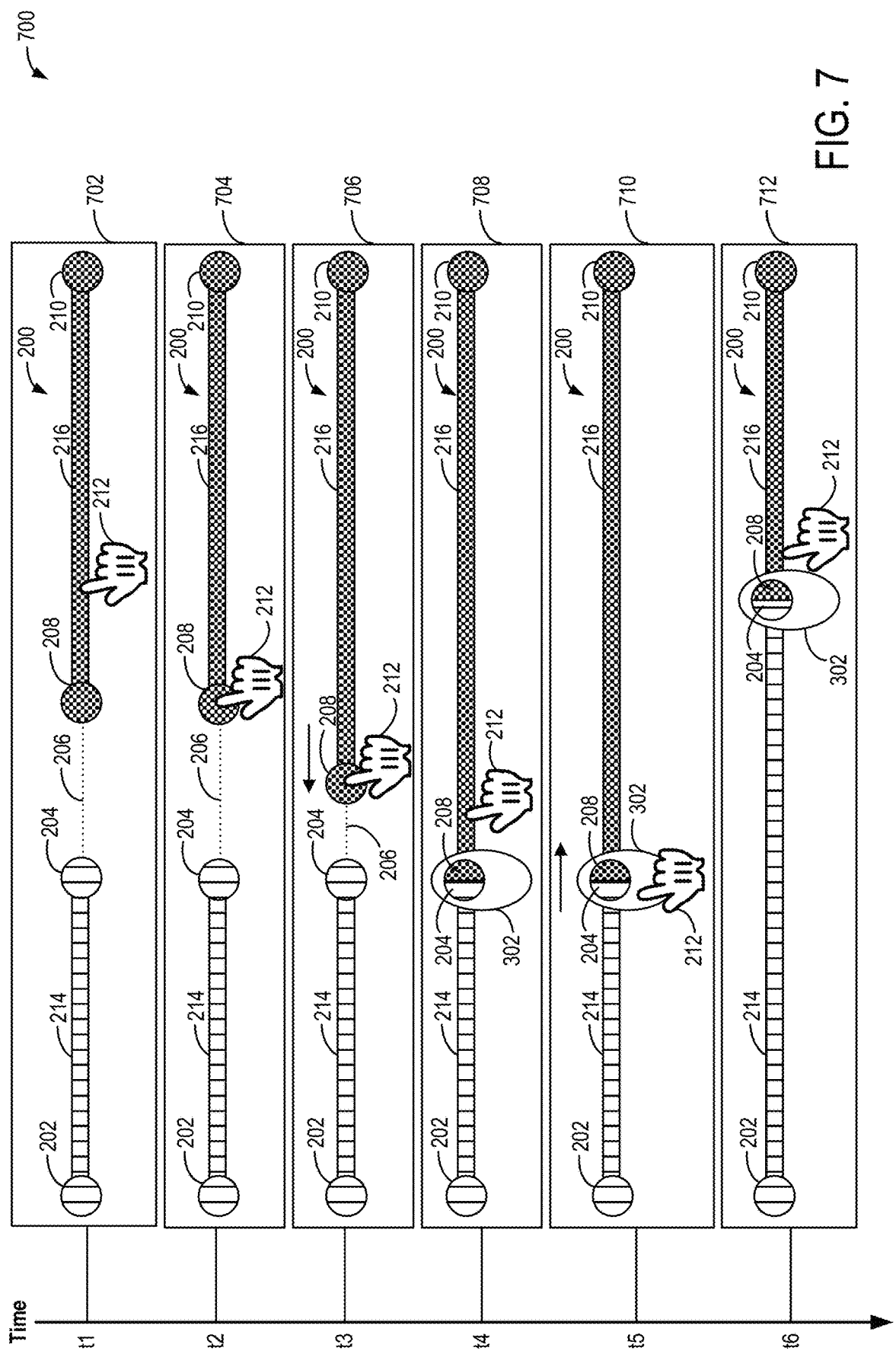
FIG. 7 shows an example of a slider thumb linking operation for two ranges based on inputs received via a user interface.
Figure 8:
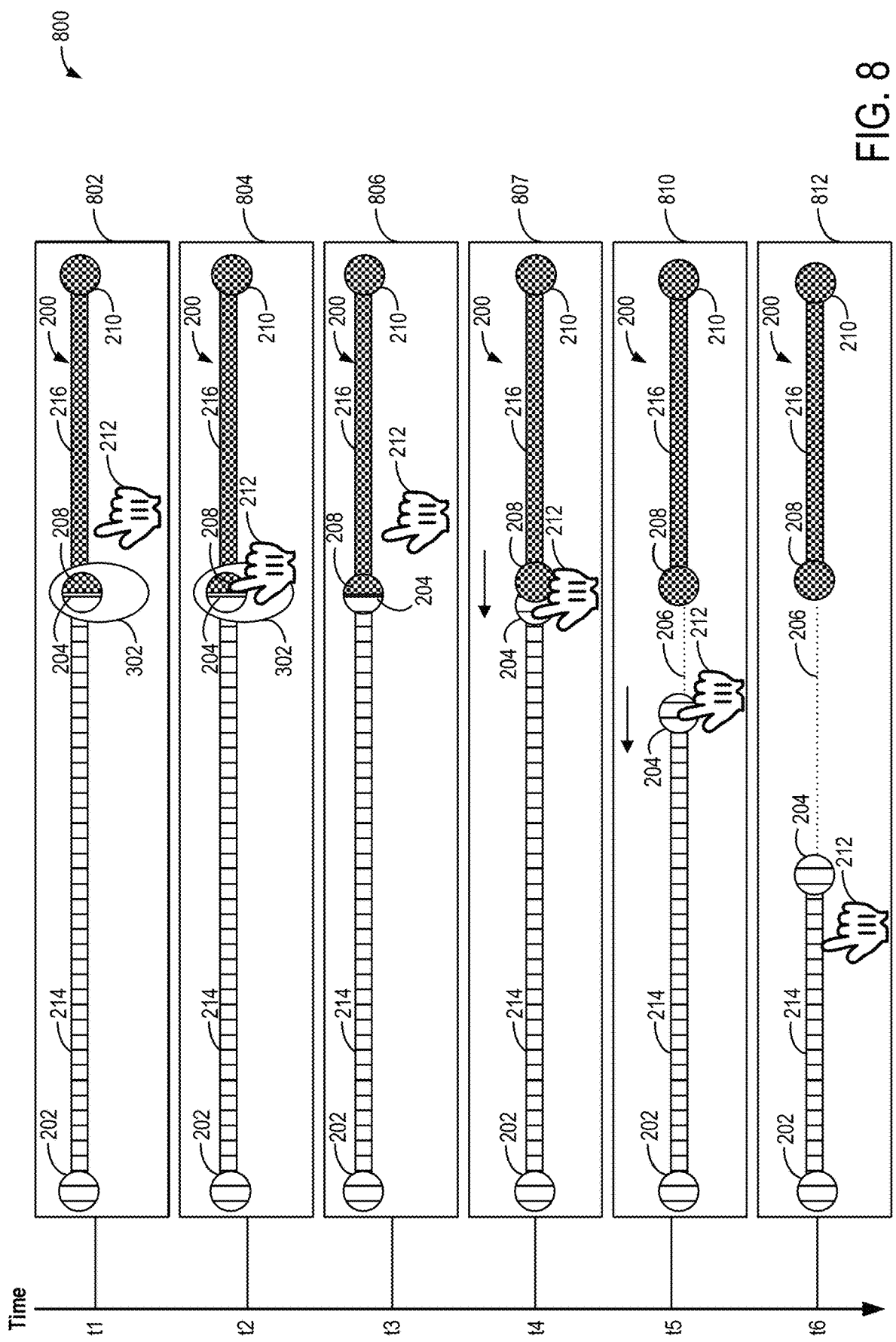
FIG. 8 shows an example of a slider thumb unlinking operation for two ranges based on inputs received via a user interface.
Figure 9:
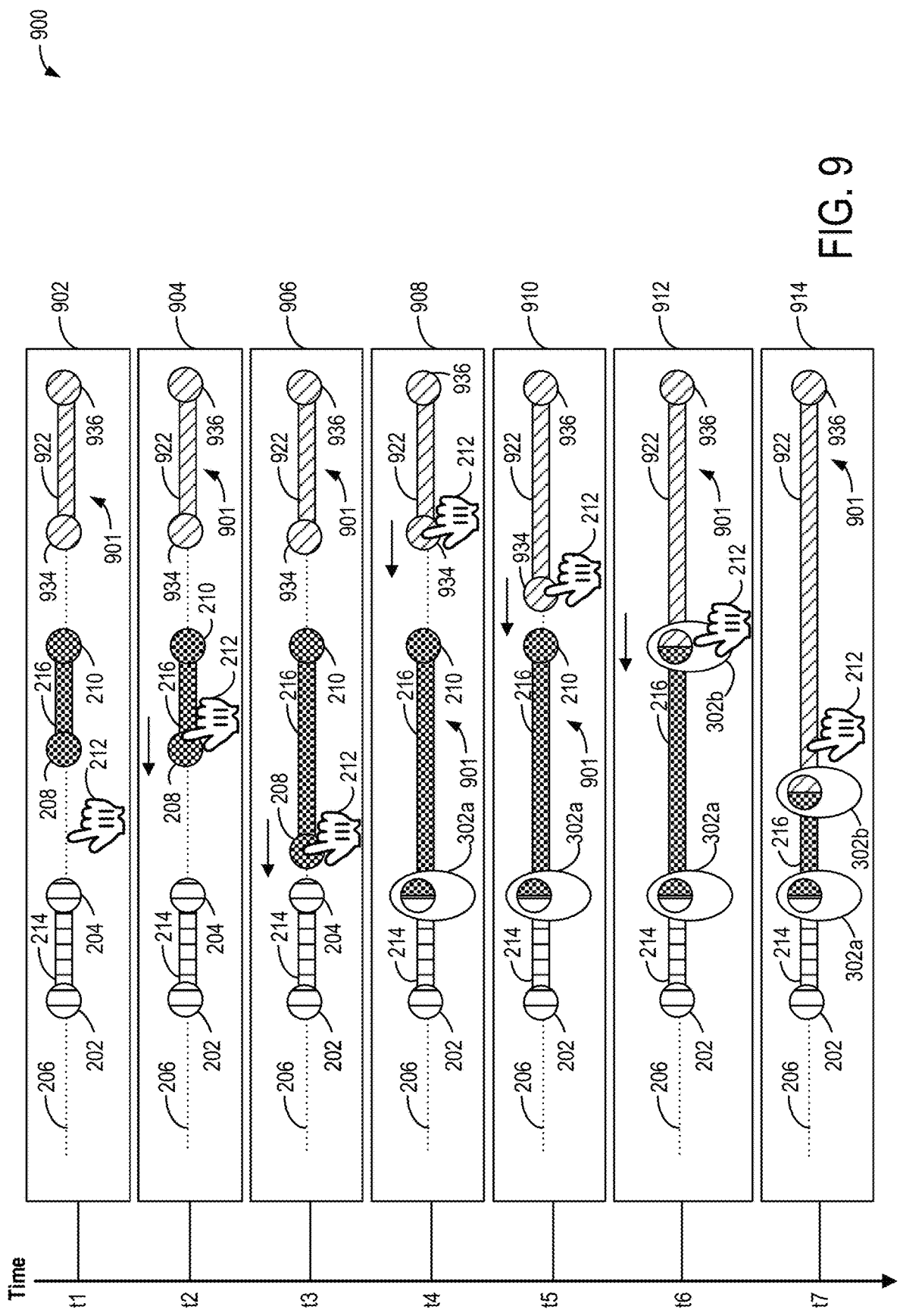
FIG. 9 shows an example of a slider thumb linking operation for more than two ranges based on inputs received via a user interface.
Figure 10:
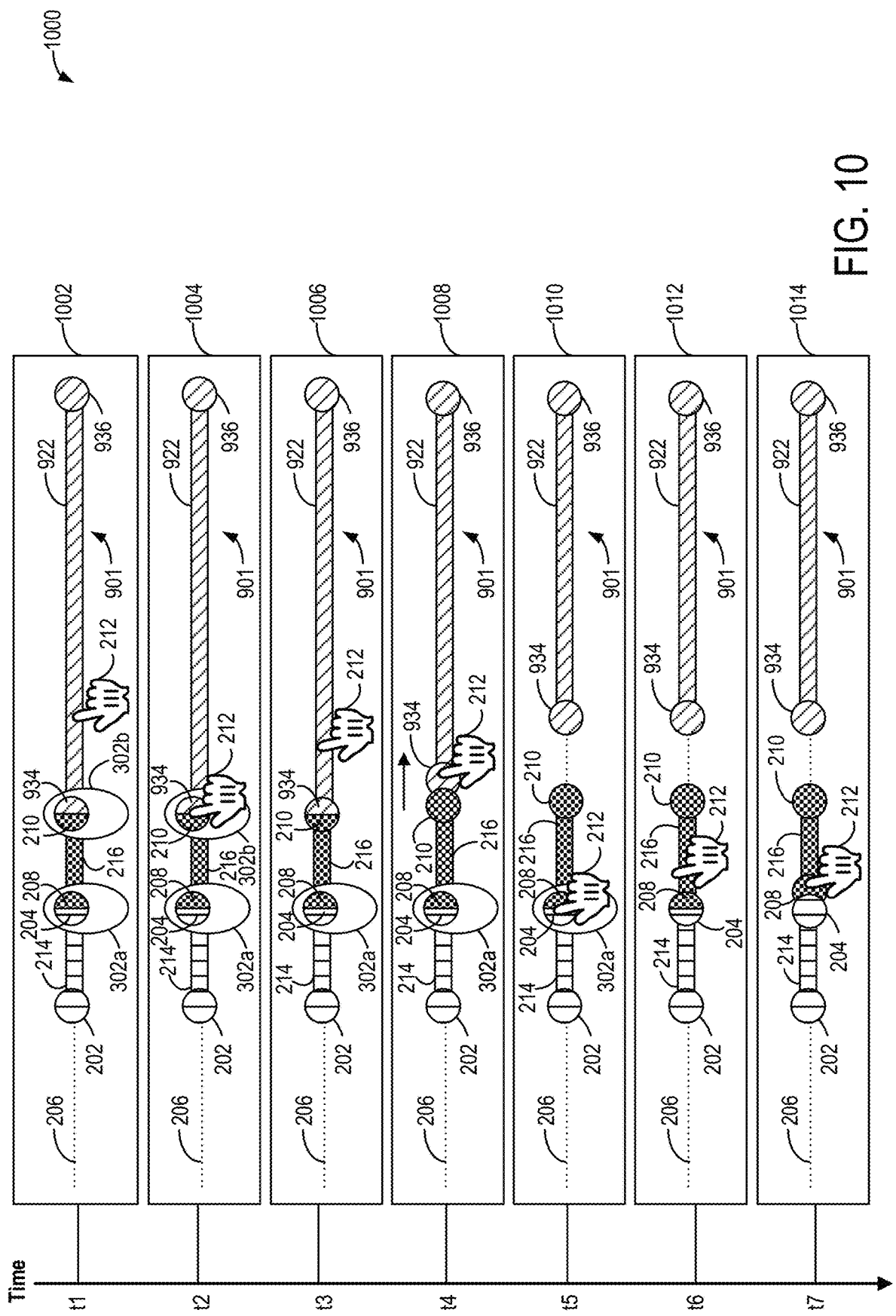
FIG. 10 shows an example of a slider thumb unlinking operation for more than two ranges based on inputs received via a user interface.
Figure 11:
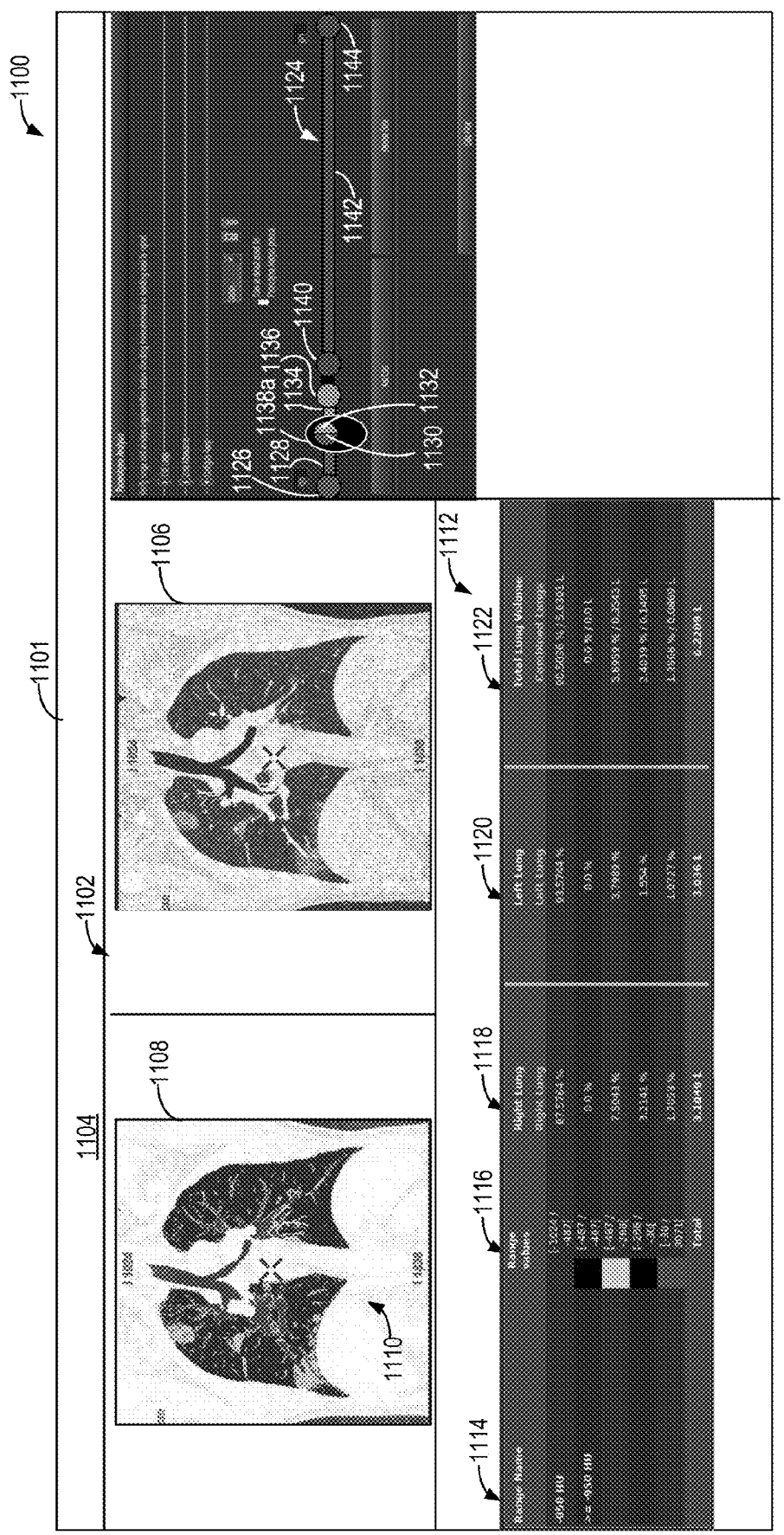
FIG. 11 shows a first embodiment of a user interface of an imaging system including a slider bar for adjusting a medical imaging output.
Figure 12:
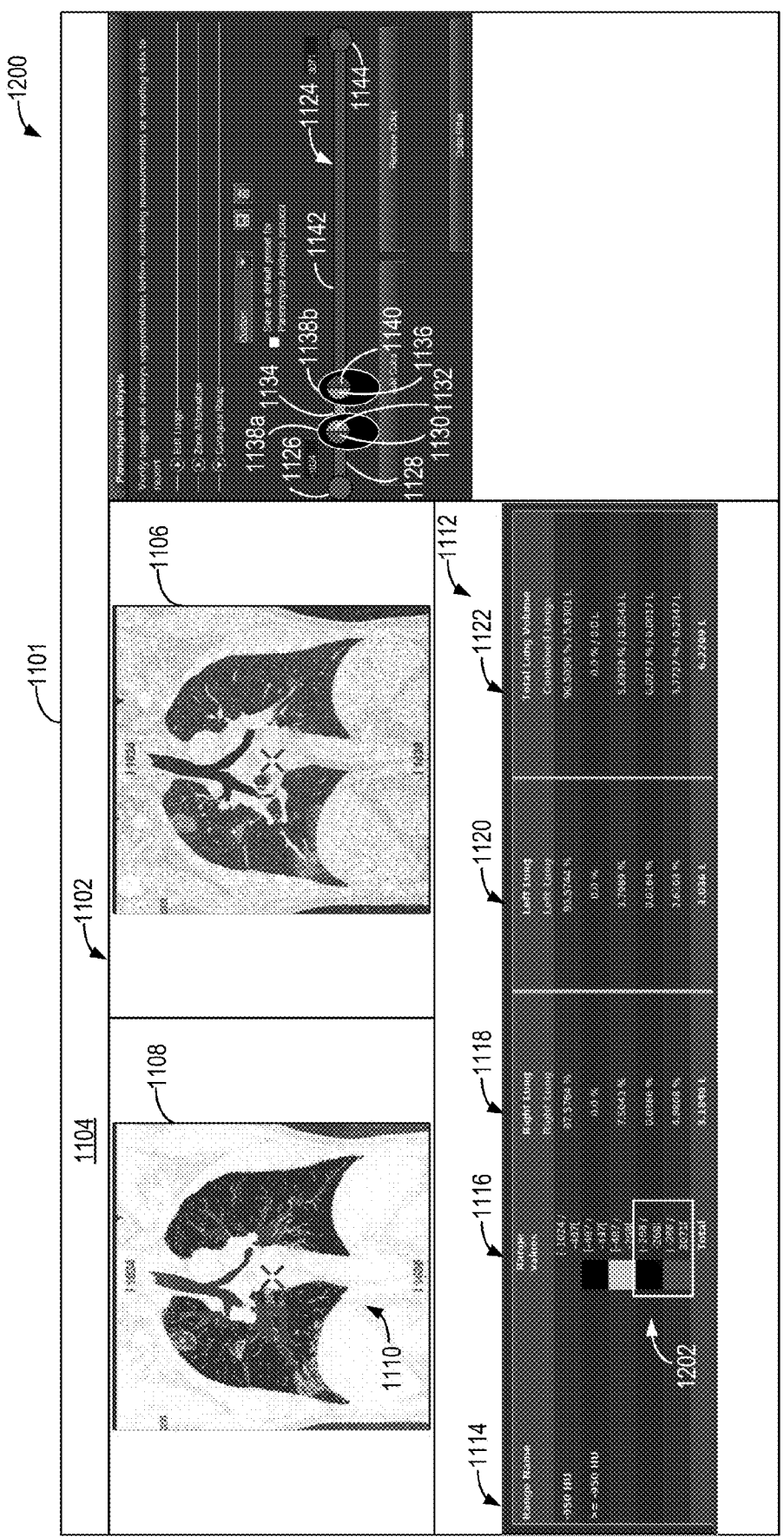
FIG. 12 shows a first example adjustment to the medical imaging output of FIG. 11 based on inputs received via the slider bar.
Figure 13:
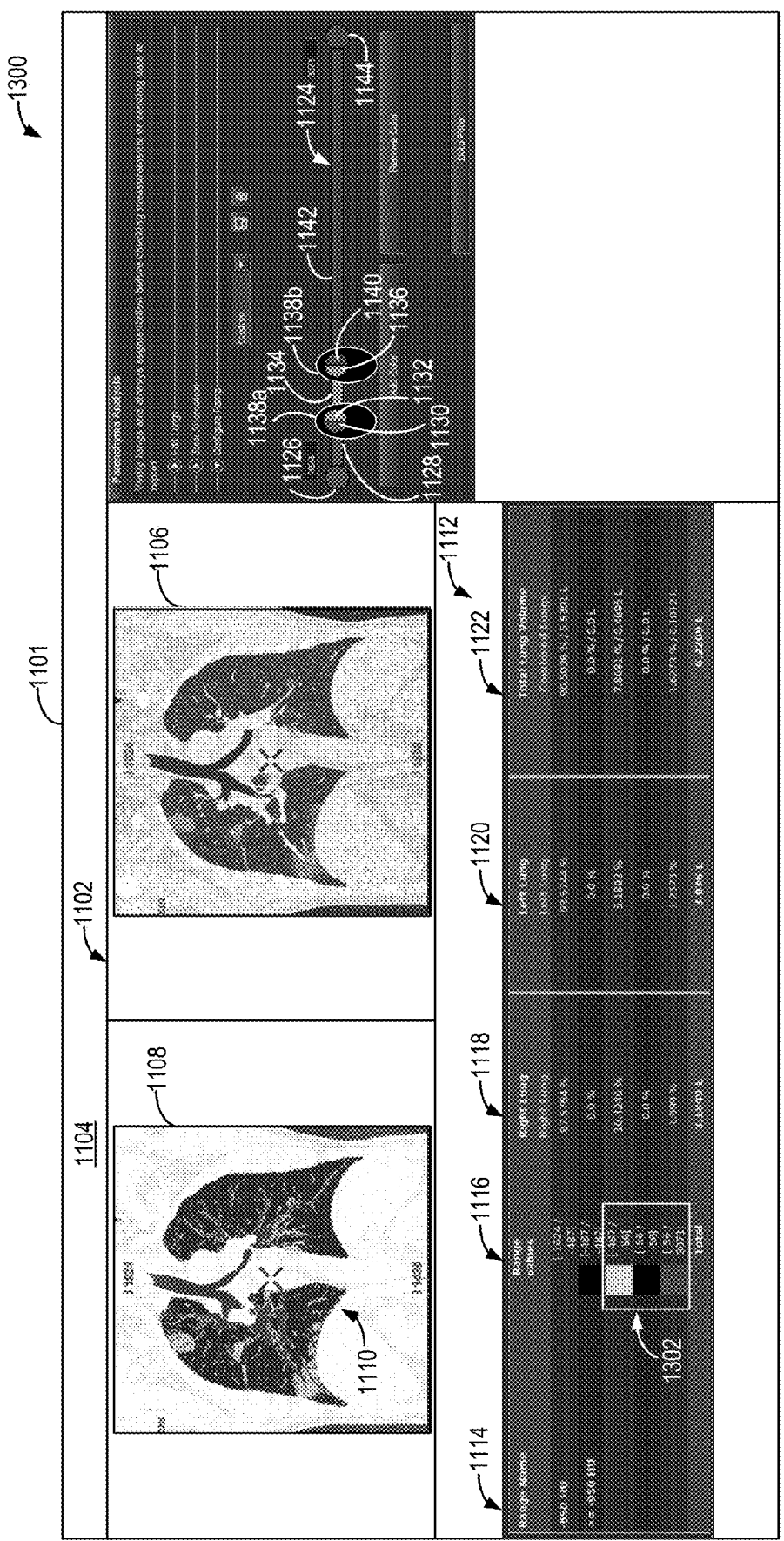
FIG. 13 shows a second example adjustment of the medical imaging output of FIG. 11 based on inputs received via the slider bar.
Figure 14:
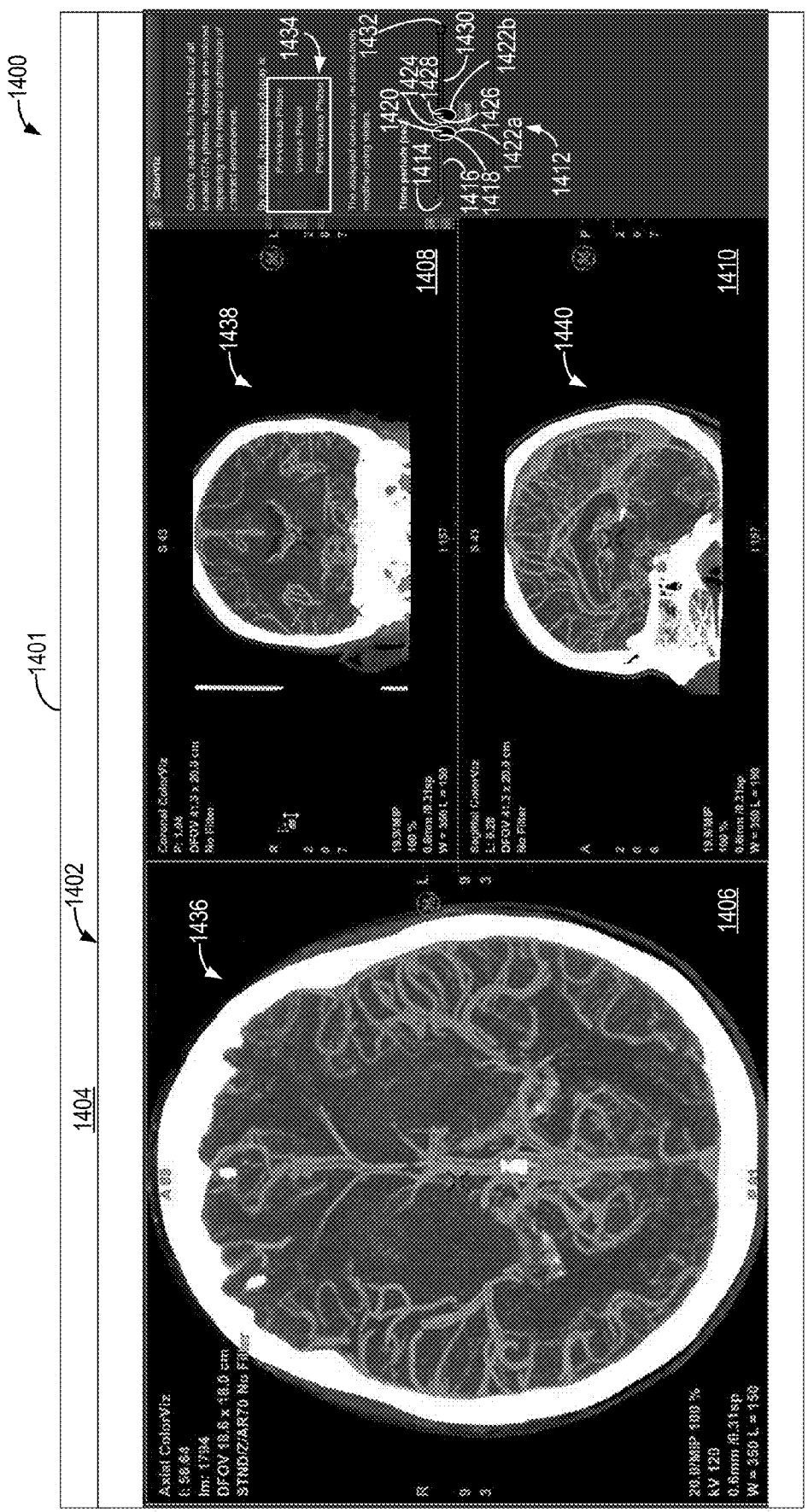
FIG. 14 shows a second embodiment of a user interface of an imaging system including a slider bar for adjusting a medical imaging output.
Figure 15:
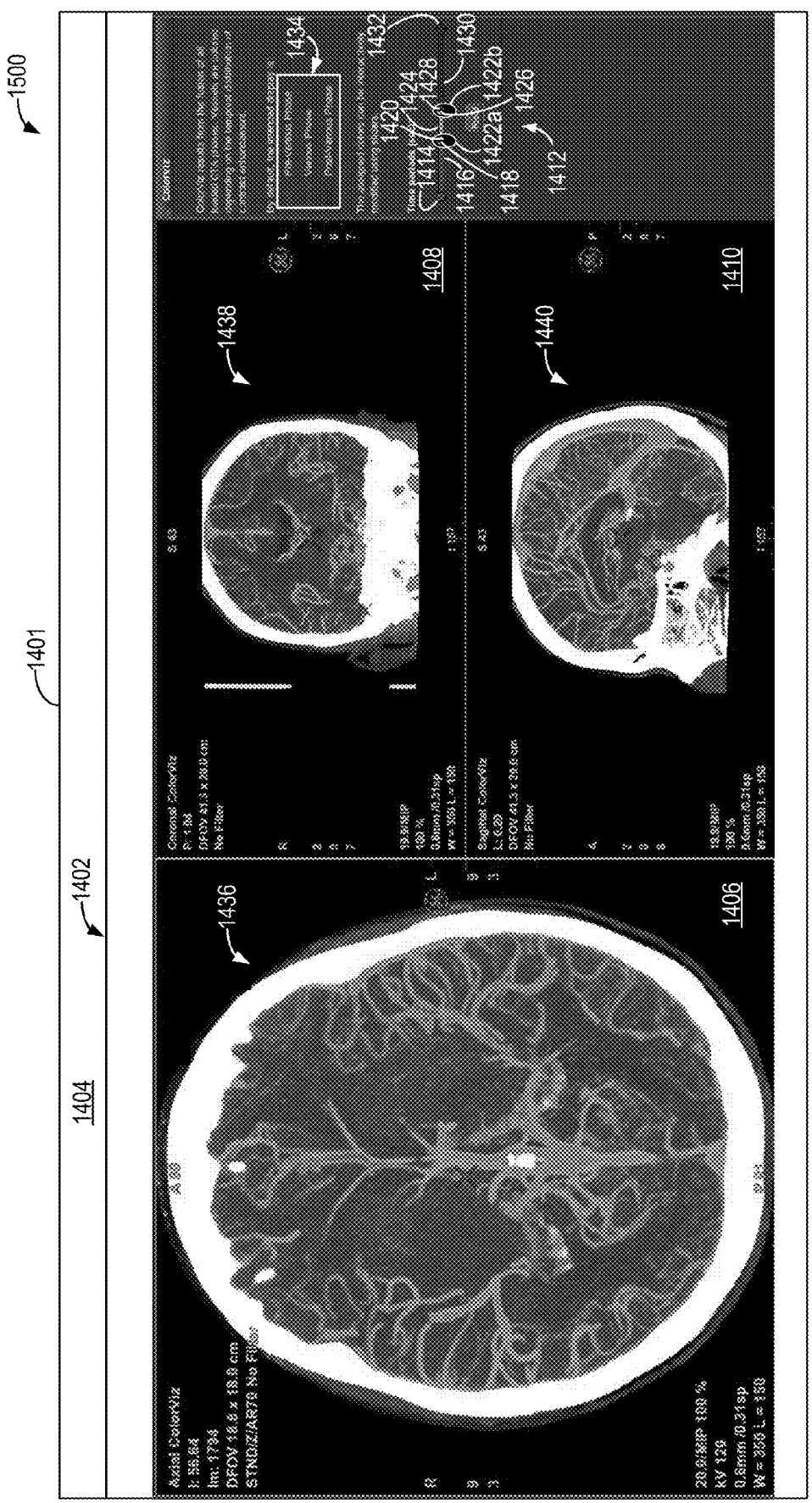
FIG. 15 shows a first example adjustment of the medical imaging output of FIG. 14 based on inputs received via the slider bar.
Figure 16:
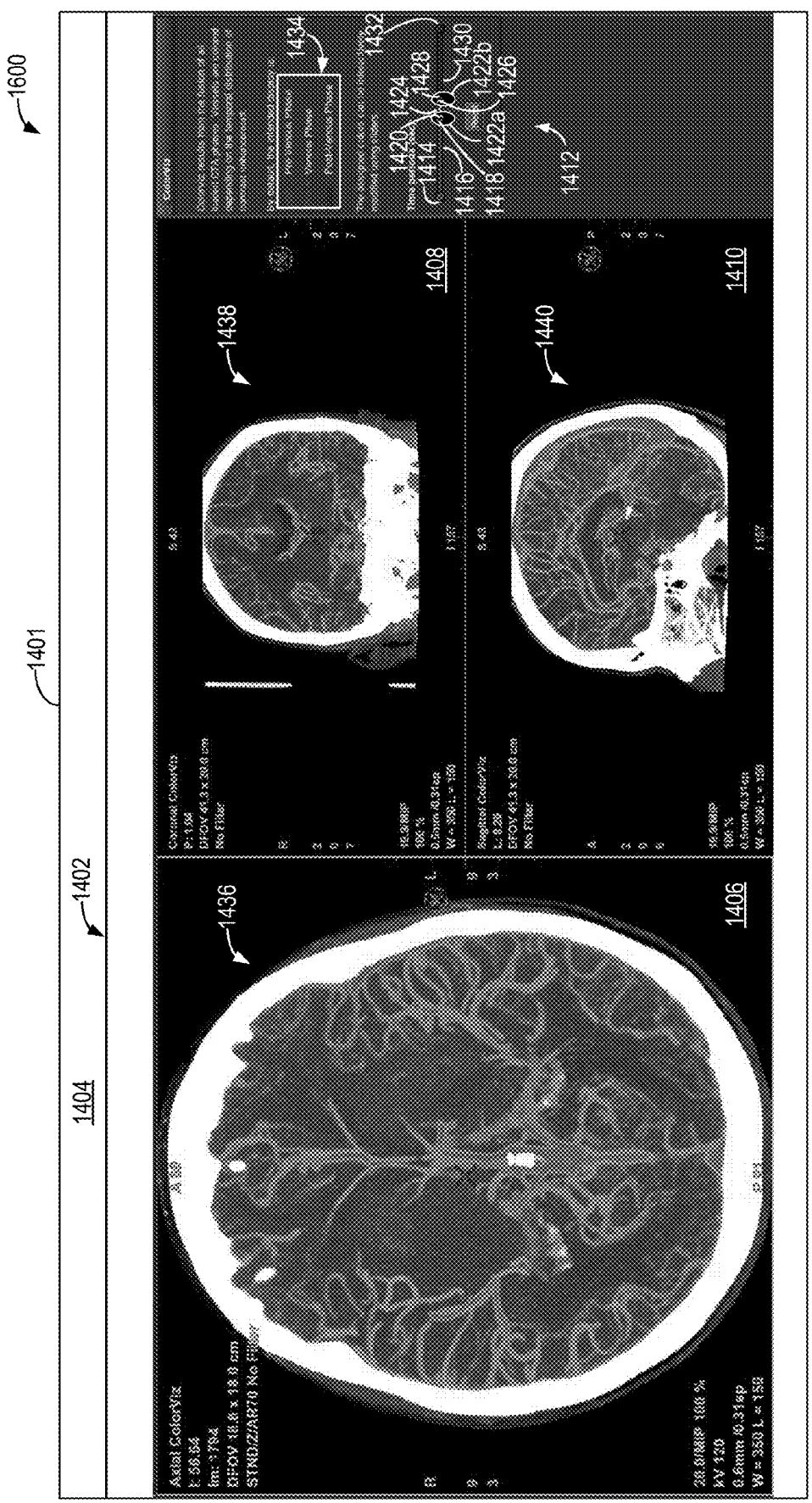
FIG. 16 shows a second example adjustment of the medical imaging output of FIG. 14 based on inputs received via the slider bar.

The multi-range slider may be used to adjust an output of an image analysis operation, such as according to the method of FIG. 6, with a selected operating mode of the multi-range slider resulting in different adjustments to the output. FIG. 7 illustrates an example sequence of the linking of two adjacent ranges and adjusting the ranges in tandem via the slider handle, while FIG. 8 illustrates an example sequence of unlinking the two adjacent ranges. FIG. 9 illustrates an example sequence of the linking of two or more adjacent ranges via the user interface. FIG. 10 illustrates an example sequence of the unlinking of two or more adjacent ranges via the user interface. An example of the user interface is shown in FIG. 11, which includes a multi-range slider that may be used to adjust an image segmentation output of a lung image of a patient. The image signal values may be adjusted on the user interface via the slider operating modes described herein to adjust the image segmentation output of the lung image as illustrated in FIGS. 12 and 13. A second example of the user interface is shown in FIG. 14, which includes a multi-range slider that may be used to adjust contrast enhancement phase mapping for a computed tomography angiography (CTA) scan of a brain of a patient. FIGS. 15 and 16 illustrate adjusting time periods on the user interface via the slider operating modes described herein to adjust the contrast enhancement phase mapping.

Advantages that may be realized in the practice of some embodiments of the described systems and methods are that defining the ranges may become less time intensive and may reduce user error. As described herein, when the thumbs are linked, dependent movement of the linked thumbs enables the thumbs to be moved simultaneously, which eliminates the repeating steps of adjusting each thumb to the same value separately. Further, the systems and methods described herein reduce the extent of user input used to define the ranges. By decreasing the amount of user input used, the potential for user error is decreased. Overall, more accurate ranges may be defined more quickly, which may decrease an amount of time it takes the user to evaluate a medical image.

Other advantages of operating a slider in the linked mode may include increasing an efficiency of a computing device. For example, operation of the slider in the linked mode may allow the computing device to adjust multiple (e.g., two) slider ranges or other widgets of the user interface based on a single user input. Running time of an algorithm (e.g., an algorithm that controls the user interface) may be reduced when a plurality of widgets is adjusted in response to the single user input compared to adjusting the plurality of widgets based on a plurality of user inputs. As such, the algorithmic efficiency of the computing device may be increased by selectively operating the slider in the linked mode.

Referring now to FIG. 1, an example medical image processing system 100 is shown. In some embodiments, the medical image processing system 100 is incorporated into a medical imaging system, such as an ultrasound imaging system, a magnetic resonance imaging (MRI) system, a computed tomography (CT) system, a single-photon emission computed tomography (SPECT) system, and the like. In some embodiments, at least a portion of the medical image processing system 100 is disposed at a device (e.g., an edge device or server) communicably coupled to the medical imaging system via wired and/or wireless connections. In some embodiments, the medical image processing system 100 is disposed at a separate device (e.g., a workstation) that can receive images from the medical imaging system or from a storage device that stores the images generated by the medical imaging system. The medical image processing system 100 may comprise an image processor 110 and a user interface 130. For example, the image processor 110 may be operatively/communicatively coupled to the user interface 130.

The image processor 110 includes a processor 102 configured to execute machine readable instructions stored in a non-transitory memory 104. The processor 102 may be single core or multi-core, and the programs executed by the processor 102 may be configured for parallel or distributed processing. In some embodiments, the processor 102 may optionally include individual components that are distributed throughout two or more devices, which may be remotely located and/or configured for coordinated processing. In some embodiments, one or more aspects of the processor 102 may be virtualized and executed by remotely-accessible networked computing devices configured in a cloud computing configuration. In some embodiments, the processor 102 may include other electronic components capable of carrying out processing functions, such as a digital signal processor, a FPGA, or a graphics board. In some embodiments, the processor 102 may include multiple electronic components capable of carrying out processing functions. For example, the processor 102 may include two or more electronic components selected from a plurality of possible electronic components, including a central processor, a digital signal processor, a field-programmable gate array, and a graphics board. In still further embodiments, the processor 102 may be configured as a graphical processing unit (GPU), including parallel computing architecture and parallel processing capabilities.

As illustrated in FIG. 1, in some embodiments, the non-transitory memory 104 stores a medical image analysis module 106 and medical image data 108. The medical image analysis module 106 includes one or more algorithms, including machine learning models, to process input medical images from the medical image data 108. In some examples, the medical image analysis module 106 may provide an artificial intelligence system for identifying different tissue types and/or anatomical features (e.g., lesions or vessels) within the medical image data 108. For example, the medical image analysis module 106 may include one or more deep learning networks comprising a plurality of weights and biases, activation functions, loss functions, gradient descent algorithms, and instructions for implementing the one or more deep learning networks to process the input medical images. Additionally or alternatively, the medical image analysis module 106 may store instructions for implementing a neural network, such as a convolutional neural network, for identifying the different tissues types and/or anatomical features captured in the medical image data 108. The medical image analysis module 106 may include trained and/or untrained neural networks and may further include training routines, or parameters (e.g., weights and biases), associated with one or more neural network models stored therein. Additionally or alternatively, the medical image analysis module 106 may include image recognition algorithms, shape or edge detection algorithms, and the like for identifying the different tissues types and/or anatomical features.

The medical image analysis module 106 may include conventionally programmed algorithms in addition to or as an alternative to the machine learning-based algorithms described above. For example, the medical image analysis module 106 may store instructions for implementing one or more pre-programmed transformations, manipulations, and/or adjustments to the input medical image data 108. Further, the medical image analysis module 106 may include instructions for outputting an analysis image or report based on the conventional and/or machine learning-based evaluation of the medical image data.

In some embodiments, the medical image analysis module 106 may evaluate the medical image data 108 as it is acquired in real-time. As used herein, the term "real-time" is defined to include a procedure that is performed without any intentional delay (e.g., substantially at the time of occurrence). Additionally or alternatively, the medical image analysis module 106 may evaluate the medical image data 108 offline, not in real-time.

In some embodiments, the medical image analysis module 106 may further include trained and/or untrained neural networks for identifying and differentiating anatomical features in the medical image data 108. For example, the anatomical features identified via the trained and/or untrained neural networks may include organs, tissues, vessels, and the like. In one embodiment, the neural network may be trained using medical images (e.g., images generated from a CT scan). After training, a transformed medical image may be generated by the neural network directly from the medical images, which may include segmentation to differentiate different types of tissues, types of lesions, or temporal phases of contrast dye uptake (e.g., for computed tomography angiography scan).

In some embodiments, the image processor 110 may be communicatively coupled to a training module 120, which includes instructions for training one or more of the machine learning models stored in the medical image analysis module 106. The training module 120 may include instructions that, when executed by a processor, cause the processor to build a model (e.g., a mathematical model) based on sample data to make predictions or decisions regarding medical images without the explicit programming of a conventional algorithm that does not utilize machine learning. In one example, the training module 120 includes instructions for receiving training data sets from the medical image data 108. The training data sets comprise sets of medical images, associated ground truth labels/images, and associated model outputs for use in training one or more of the machine learning models stored in the medical image analysis module 106. The training module 120 may receive medical images, associated ground truth labels/images, and associated model outputs for use in training the one or more machine learning models from sources other than the medical image data 108, such as other image processing systems, the cloud, etc. In some embodiments, one or more aspects of the training module 120 may include remotely-accessible networked storage devices configured in a cloud computing configuration. Further, in some embodiments, the training module 120 is included in the non-transitory memory 104. Additionally, or alternatively, in some embodiments, the training module 120 may be used to generate the medical image analysis module 106 offline and remote from the medical image processing system 100. In such embodiments, the training module 120 may not be included in the medical image processing system 100 but may generate data stored in the medical image processing system 100. For example, the medical image analysis module 106 may be pre-trained with the training module 120 at a place of manufacture.

The medical image processing system 100 may further include the user interface 130. The user interface 130 may comprise a display device 132 and a user input device 134. The display device 132 may include one or more display devices utilizing any type of display technology. In some embodiments, the display device 132 may comprise a computer monitor and may display unprocessed images, processed images, parametric maps, and/or exam reports. The display device 132 may be combined with the processor 102, the non-transitory memory 104, and/or the user input device 134 in a shared enclosure or may be a peripheral display device. The display device 132 may include a monitor, a touchscreen, a projector, or another type of display device, which may enable a user to view medical images and/or interact with various data stored in the non-transitory memory 104. In some embodiments, the display device 132 may be included in a smartphone, a tablet, a smartwatch, or the like.

The user input device 134 may comprise one or more of a touchscreen, a keyboard, a mouse, a trackpad, a motion sensing camera, or other device configured to enable a user to interact with and manipulate data stored within the image processor 110. As an example, the user input device 134 may enable a user to select images for analysis by the medical image analysis module 106. In some embodiments, such as touchscreen embodiments, the user input device 134 is integrated with the display device 132.

The non-transitory memory 104 may further comprise a user interface control module 112. The user interface control module 112 may store instructions for controlling components of the user interface 130, such as the components described herein with reference to FIGS. 2-3. For example, the user interface control module 112 may include instructions for operating thumbs of a slider bar in one of a linked mode and an unlinked mode as well as instructions for transitioning between the linked mode and the unlinked mode, such as the methods described herein with respect to FIGS. 4 and 5. As one example, the user interface control module 112 may include instructions that enable automatic linking/unlinking or manual linking/unlinking of the thumbs of the slider bar in response to receiving pre-determined user inputs via the user input device 134. Additionally or alternatively, the user interface control module 112 may include instructions for interfacing with the medical image analysis module 106 so that adjustments made to the thumbs of the slider bar are reflected in an output of the medical image analysis module 106 displayed via the display device 132.

The non-transitory memory 104 further stores the medical image data 108. The medical image data 108 includes, for example, functional and/or anatomical images captured by an imaging modality, such as ultrasound imaging systems, MRI systems, CT systems, and so forth. As one example, the medical image data 108 may include CT images, such as thoracic CT images. Further, the medical image data 108 may include one or more of 2D images, 3D images, static single frame images, and multi-frame cine-loops (e.g., movies).

In some embodiments, the non-transitory memory 104 may include components disposed at two or more devices, which may be remotely located and/or configured for coordinated processing. In some embodiments, one or more aspects of the non-transitory memory 104 may include remotely-accessible networked storage devices in a cloud computing configuration. As one example, the non-transitory memory 104 may be part of a picture archiving and communication system (PACS) that is configured to store patient medical histories, imaging data, test results, diagnosis information, management information, and/or scheduling information, for example.

It may be understood that the medical image processing system 100 shown in FIG. 1 is one non-limiting embodiment of an image processing system, and other imaging processing systems may include more, fewer, or different components without departing from the scope of this disclosure. Further, in some embodiments, at least portions of the medical image processing system 100 may be included in a medical imaging system.

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally, or alternatively, one or more of these devices may be hard-wired with logic circuits to perform these operations.

In reference to FIG. 2, a multi-range slider 200 is shown that may be displayed on the user interface 130 introduced in FIG. 1. The multi-range slider 200 comprises a track 206 (represented by a dotted line) having a fixed range of values, a first range 214 (represented by a vertical line pattern) comprising a first adjustable portion of the fixed range of values, a second range 216 (represented by a checkerboard pattern) comprising a second adjustable portion of the fixed range of values, and a plurality of thumbs that define values on the track 206, as will be elaborated below. The fixed range of values increases from left to right such that the values of the second range 216 are higher than the values of the first range 214. The portions of the track 206 that are not overlapping with the first range 214 and the second range 216 are regions of values that are not included in the first range 214 or second range 216.

A first thumb 202 defines a minimum value of the first range 214, a second thumb 204 defines a maximum value of the first range 214, a third thumb 208 defines a minimum value of the second range 216, and a fourth thumb 210 defines a maximum of the second range 216. Values included in the first range 214 and the second range 216 may be adjusted via adjustments to positions of the corresponding thumb(s) on the track 206. A cursor 212 (or other user interface visual component) may be used to select one of the first thumb 202, the second thumb 204, the third thumb 208, and the fourth thumb 210 and adjust the position of the selected thumb on the track 206. For example, the maximum value of the first range 214 may be increased in response to receiving, via the cursor 212, the selection of the second thumb 204 and adjustment of the second thumb 204 to a position that is further to the right on the track 206 (e.g., toward the third thumb 208). As another example, the maximum value of the first range 214 may be decreased in response to receiving, via the cursor 212, the selection of the second thumb 204 and adjustment of the second thumb 204 to a position that is further to the left on the track 206 (e.g., toward the first thumb 202). As still another example, the minimum value of the first range 214 may be increased in response to receiving, via the cursor 212, the selection of the first thumb 202 and adjustment of the first thumb 202 to a position that is further to the right on the track 206 (e.g., toward the second thumb 204). As yet another example, the minimum value of the first range 214 may be decreased in response to receiving, via the cursor 212, the selection of the first thumb 202 and adjustment of the first thumb 202 to a position that is further to the left on the track 206. The minimum value and the maximum value of the second range 216 may be adjusted similarly in response to receiving an adjustment to the third thumb 208 or the fourth thumb 210, respectively.

Other sequences of adjustments and operating modes of similar multi-range sliders are described below with respect to FIGS. 7-10. Further, it may be understood that other embodiments of the multi-range slider 200 may include alternative display outputs and/or numbers of adjacent ranges. One such alternative may include a vertical representation of the track 206 instead of the horizontal representation of the track 206 shown in FIG. 2. Another alternative may include a non-linear shape of the track 206 instead of the linear shape of the track 206 shown in FIG. 2. For example, the track 206 may alternatively comprise arched or curved shape.

Turning now to FIG. 3, an embodiment of a slider handle 302 is shown. The slider handle 302 may be output via a user interface (e.g., the user interface 130 of FIG. 1) while operating a slider bar in a linked mode, as will be elaborated below. The slider handle 302 comprises a linked thumb 304, which further includes a first thumb 306 of a first range maximum and a second thumb 308 of a second range minimum as a single unit that defines a single position on a track of the slider bar (e.g., the track 206 of FIG. 2). As such, the first thumb 306 and the second thumb 308 share the same position and same single, corresponding value on the track when included in the linked thumb 304. The slider handle 302 is an interactive user interface component configured to operatively couple the first thumb 306 and the second thumb 308 (e.g., as the linked thumb 308), wherein the position of both thumbs may be adjusted simultaneously via adjustment of the slider handle 302. In particular, the position of the slider handle 304 may be adjusted when the user interface receives user input within a first region 310, as indicated by dashed lines. The first region 310 may also be referred to herein as a first touch zone. For example, the user interface may receive input at the first region 310 that adjusts the position of the slider handle 304 along the track, which may adjust the single position of the linked thumb 304 and thus the single value of both of the first range maximum and second range minimum accordingly. Operating in the linked mode will be further described below with respect to FIGS. 4-6.

In contrast, the linked thumb 304 may be unlinked so that the position of the first thumb 306 and the second thumb 308 may be adjusted independently of each other when the user interface receives user input in a second region 312 (e.g., a second touch zone or unlinking touch zone), also denoted by dashed lines, at least in some embodiments. For example, the slider handle 302 may be hidden in response to receiving an unlinking request (e.g., via the second region 312), and the first thumb 306 and the second thumb 308 may no longer be included in the linked thumb 304. Upon unlinking, the slider bar is operated in an unlinked mode, where the first thumb 306 and the second thumb 308 may be individually adjusted to different positions, and thus different corresponding values for the first range maximum and second range minimum, on the track. Operating in the unlinked mode also will be further described below with respect to FIGS. 4-6. Thus, the first region 310 and the second region 312 may define portions of the slider handle 302 that may trigger different actions in response to received user input.

It may be understood that although the slider handle 302 is shown as having an elliptical (e.g., oval) shape in FIG. 3, the slider handle 302 may appear on the user interface as shapes other than the ellipse, including geometric and non-geometric shapes. For example, the slider handle 302 may have a rectangular shape. Likewise, other embodiments of the slider handle 302 may include different portions for the first region 310 and the second region 312. In some examples, the first region 310 may include an entirety of the slider handle 302 that is not included in the second region 312, or vice versa. Further, more or fewer regions (or touch zones) may be included that trigger similar or different slider bar control responses.

Figure 4:
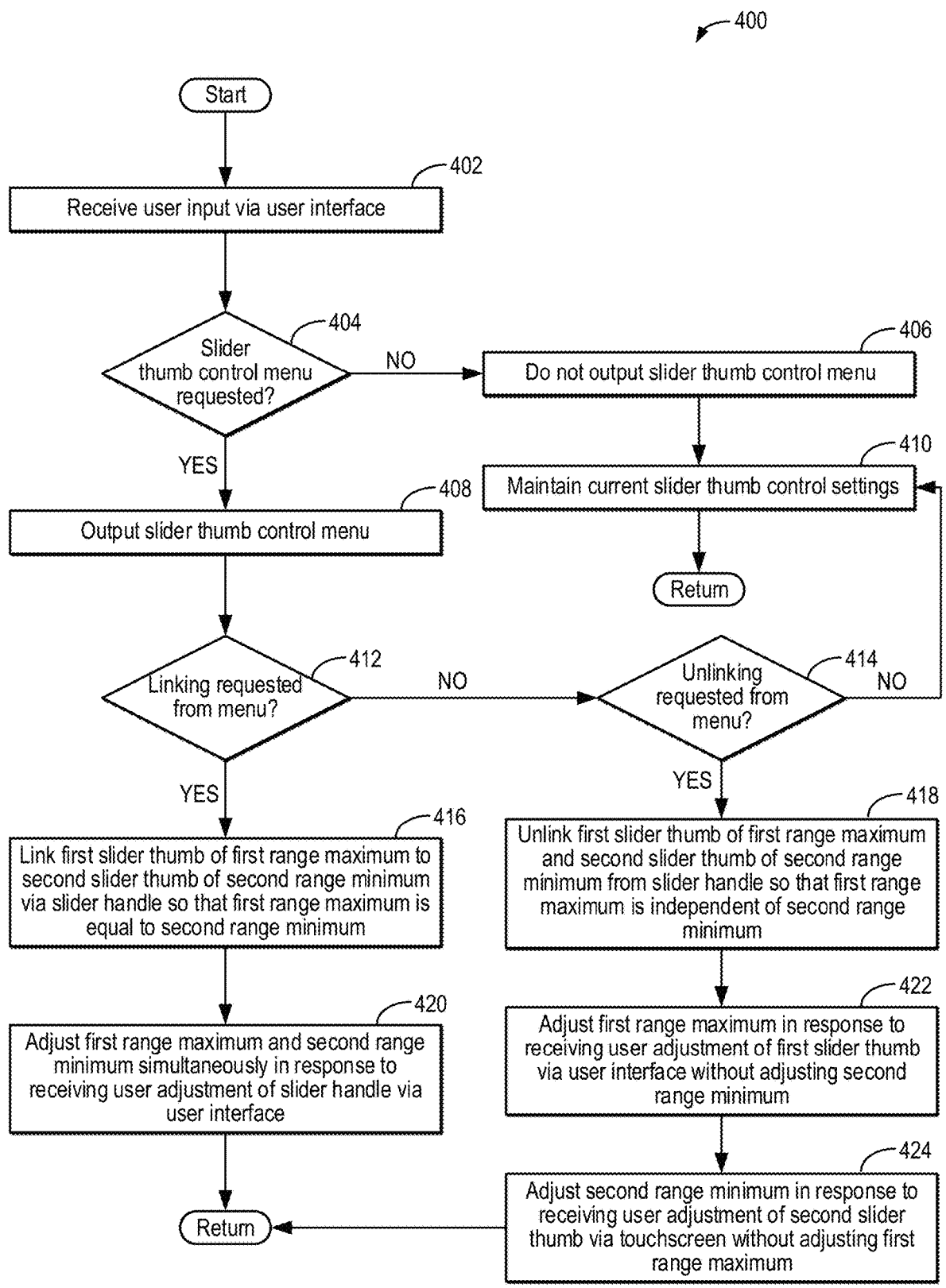
FIG. 4 is a flow chart illustrating a first example method for linking and unlinking thumbs of a slider bar.

A first example method 400 for linking and unlinking thumbs of a slider via inputs received via a user interface is shown in FIG. 4. In one embodiment, the method 400 is performed by the medical image processing system 100 of FIG. 1, and the user interface may be the user interface 130 of FIG. 1. As such, the method 400 is described with respect to the system and components described above with respect to FIGS. 1-3 but may be carried out with other systems/components without departing from the scope of this disclosure. The method 400 and the remaining methods included herein may be executed by a processor (e.g., the processor 102 of FIG. 1) according to instructions stored in non-transitory memory (e.g., the non-transitory memory 104 of FIG. 1). Although the method 400 will be described with respect to linking and unlinking a single pair of adjacent thumbs, it may be understood that the method 400 may be applied to more than one pair of adjacent thumbs. For example, a first pair of adjacent thumbs may be linked and unlinked via the method 400 independently from a second pair of adjacent thumbs, which also may be independently linked and unlinked via the method 400.

At 402, the method 400 includes receiving user input via the user interface. For example, the user input may be acquired with a user input device, such as the user input device 134 of FIG. 1, and displayed to the user via a display device, such as the display device 132 of FIG. 1. As described above with respect to FIG. 1, one or both of the user input device and the display device may be integrated with, or operatively coupled to, the user interface. For example, the user input device may include a computer mouse, a keyboard, a trackpad, or a touchscreen (e.g., a touch-sensitive display). In some examples, the user interface may include a visual component to show a current position for user interaction, such as a cursor or pointer that is controlled by the user via the user input device. For example, the user input may include the user navigating the cursor (e.g., via the user input device) to hover over or select (e.g., via clicking, tapping, dragging, or another type of pre-defined gesture) a region of interest on the user interface. In other examples, such as in some touchscreen embodiments, the user input may include direct contact with the user interface at a desired position for user interaction (e.g., via a finger touch or stylus contact with the touchscreen), and the visual component may be optionally omitted. Other types of user input may be received via the user interface in addition to the preceding examples.

Further, the user interface may include a graphical user interface (GUI), which may be output via the display and enable the user to interact with graphical icons and widgets via the user input device. The GUI may include the slider and its thumbs in addition to other interactive components. As further described below, the slider may include at least two adjacent thumbs that may be selectively linked and unlinked responsive to the received user input. An example of a slider is shown in FIG. 2 and described above (e.g., the multi-range slider 200). Further, as a result of this selective linking and unlinking, the slider may be operated in one of a linked mode and an unlinked mode, as will also be described below.

At 404, the method 400 includes determining whether a slider thumb control menu is requested (e.g., via the user input received at 402). The slider control menu may enable the selective linking and unlinking of the first thumb and the second thumb. In some examples, it may be determined that the slider thumb control menu is requested in response to receiving a pre-defined interaction at a pre-determined position on the slider and/or its thumbs. For example, the pre-defined interaction may include the cursor (or other user input device) moving to the pre-determined position. The pre-determined position may overlap with one of the thumbs and/or may be a pre-determined, non-zero threshold distance from one of the thumbs (e.g., a number of millimeters, such as a value in a range between 1 and 100 millimeters, or a number of pixels, such as a number in a range between 1 and 300 pixels). In some examples, the pre-defined interaction may further include the cursor hovering at the pre-determined position. In other examples, the pre-defined interaction may include a clicking action or other pre-programmed gesture at the pre-determined location. For example, the clicking action or other pre-programmed gesture may include right-clicking via a mouse, a two-fingered tap via a trackpad or touchscreen, or another type of pre-programmed user input.

If the slider thumb control menu is not requested, then the method 400 proceeds to 406 and includes not outputting the slider thumb control menu. Determining that the slider thumb control menu is not requested may include not receiving the pre-defined interaction at the pre-determined position on the slider and/or its thumbs. For example, the user input received may not include the cursor hovering or clicking within the pre-determined threshold distance of one of the thumbs. As such, the display device of the user interface may not output the control menu that enables the slider thumb control settings to be changed.

At 410, the method 400 includes maintaining the current slider control settings. Because the slider thumb control menu is not output, no changes may be made to the slider thumb control settings. As such, the two adjacent thumbs may continue operating in one of the linked mode and the unlinked mode based on which is currently selected. For example, if the linked mode is selected, the slider thumbs may continue to be operated in the linked mode. Alternatively, if the unlinked mode is selected, the slider thumbs may continue to be operated in the unlinked mode. Operation of the slider thumbs in the linked mode and the unlinked mode will be further described below. The method 400 may return. For example, the method 400 may be repeated so that the slider control may be adjusted in response to user input.

Returning to 404, if the slider thumb control menu is requested, the method 400 proceeds to 408 and includes outputting the slider thumb control menu. In response to the slider thumb control menu being requested, the processor may output the slider control menu via display device of the user interface to enable the slider thumb control settings to be changed. The slider thumb control menu may be a drop-down menu that offers one or more selectable slider thumb control settings. In some examples, the one or more options offered by the slider thumb control menu may change based on the currently selected settings. For example, if the slider thumbs are linked, the slider thumb control menu may offer an unlinking option. As another example, if the slider thumbs are unlinked, the slider thumb control menu may offer a linking option.

At 412, the method 400 includes determining whether linking is requested (e.g., via the user input received at 402). In one example, the processor may output, via the display device of the user interface, the linking option (or prompt) on the slider thumb control menu that asks the user or operator if the user or operator wants to enable the linked mode of operation for the slider thumbs. As such, the processor may determine that linking is requested in response to the user interface receiving user input that selects the linking option on the slider thumb control menu. For example, the user may use the cursor, a touch-based gesture, or another type of pre-programmed input to select the linking option via the user input device. As another example, the processor may determine that linking is not requested in response to the user interface receiving user input that does not select the linking option on the slider thumb control menu. In some examples, not receiving selection of the linking option may include receiving selection of a different prompt or option, such as the unlinking option (or prompt) that asks the user or operator if operating in the unlinked mode is desired, as will be elaborated below at 414. As another example, not receiving selection of the linking option may include receiving user input that closes the slider thumb control menu without selecting an option.

If the linking is requested, then the method 400 proceeds to 416 and includes linking a first slider thumb of a first range maximum (e.g., a maximum of a first range) to a second slider thumb of a second range minimum (e.g., a minimum of a second range) via a slider handle so that the first range maximum is equal to the second range minimum. As described above with respect to FIG. 3, the slider handle is a UI component that couples the position of the first slider thumb of the first range maximum and the position of the second slider thumb of the second range minimum on a track of the slider, ensuring that the first range maximum is equal to the second range minimum in value. An example sequence illustrating linking the first slider thumb and the second slider thumb will be described below with respect to FIG. 7.

At 420, the method 400 includes adjusting the first range maximum and the second range minimum simultaneously in response to receiving a user adjustment of the slider handle via the user interface. The user adjustment of the slider handle adjusts a displayed position of the first slider thumb and the second slider thumb in tandem so that the value of the second range minimum and the first range maximum share a single numerical value, as described above, and an overlapping position on the track. For example, the slider handle may surround and control a positon of a linked thumb comprising both the first thumb and the second thumb (e.g., the linked thumb 304 of FIG. 3). Adjusting the first range maximum and the second range minimum simultaneously via the slider handle is also referred to herein as operating the slider thumbs in the linked mode. An example of operating the slider thumbs in the linked mode may include the processor adjusting the displayed position and numerical value of both of the first thumb and the second thumb on the track of the slider at the same time in response to the user interface receiving a single user input (e.g., via the user input device). For example, the user interface may receive a user input that selects a pre-determined touch zone of the slider handle and drags the slider handle to decrease the first range maximum and the second range minimum or to increase the first range maximum and the second range minimum. The method 400 returns.

By operating the slider thumbs in the linked mode, an output of a medical image processing system may be more easily and accurately adjusted in real-time or near real-time based on the user input received at the user interface. In one such example, the processor may update a displayed segmentation output that may use colors or fill patterns to differentiate regions of an imaged organ on the graphical user interface as a result of an increase (or decrease) in the number of pixels of a particular color or fill pattern associated with both of the first range and the second range in response to receiving a simultaneous adjustment of the first range the second range via the slider handle, as will be elaborated below with respect to FIG. 6. Examples of real-time adjustments of the output due to the adjustment of linked slider thumbs are illustrated in FIGS. 12-16.

Returning to 412, if the linking is not requested, then the method 400 proceeds to 414 and determines whether unlinking is requested (e.g., via the user input received at 402). In one example, the processor may output, via the display device of the user interface, the unlinking option on the slider thumb control menu that asks the user or operator if the user or operator wants to enable the unlinked mode of operation for the slider thumbs. As such, the processor may determine that the unlinking is requested in response to the user interface receiving user input that selects the unlinking option on the slider thumb control menu. In particular, the user may use the cursor, a touch-based gesture, or another type of pre-programmed input to select the unlinking option via the user input device. As another example, the processor may determine that unlinking is not requested in response to the user interface receiving user input that does not select the unlinking option on the slider thumb control menu. In other examples, not receiving selection of the unlinking option may include receiving selection of a different prompt or action, such as receiving selection of the linking option, as described above at 412. Another example of not receiving selection of the unlinking option may include receiving user input that closes the slider thumb control menu without selecting an option.

If the unlinking is requested, the method 400 proceeds to 418 and includes unlinking the first slider thumb of the first range maximum and the second slider thumb of the second range minimum from the slider handle so that the first range maximum is independent of the second range minimum. For example, unlinking the first slider thumb and the second slider thumb from the slider handle may include no longer displaying the slider handle on the user interface. Further, the linked thumb comprising both of the first thumb and the second thumb may no longer be displayed, and instead, the first thumb and the second thumb may be displayed as separate graphical components. The slider handle may not be accessible to the user once the first thumb of the first range maximum and the second thumb of the second range maximum are unlinked. An example sequence illustrating unlinking the first slider thumb and the second slider thumb will be described below with respect to FIG. 9.

At 422, the method 400 includes adjusting the first range maximum in response to receiving a user adjustment of the first slider thumb via the user interface without adjusting the second range minimum. For example, receiving the user adjustment of the first slider thumb may result in the displayed position of the first slider thumb and the corresponding numerical value of the first range maximum being adjusted (e.g., changed) in real-time while the displayed position of the second slider thumb and the corresponding numerical value of the second range minimum are maintained and not changed. Thus, the first slider thumb and the second slider thumb may be adjusted independently, also referred to herein as operating the slider in the unlinked mode. An example of operating the slider thumbs in the unlinked mode may include the processor adjusting the displayed position and numerical value of the first thumb, and not the second thumb, in response to receiving user input (e.g., via the user input device) that selects the first thumb on the track and adjusts the position of the first thumb to increase or decrease the first range maximum without affecting the second range minimum.

At 424, the method 400 includes adjusting the second range minimum in response to receiving a user adjustment of the second slider thumb via the user interface without adjusting the first range slider maximum. As an example, receiving the user adjustment of the second slider thumb may result in the displayed position of the second slider thumb and the corresponding numerical value of the second range minimum being adjusted (e.g., changed) in real-time while the displayed position of the first slider thumb and the corresponding numerical value of the first range maximum are maintained. Therefore, an example of operating the slider thumbs in the unlinked mode may include the processor adjusting the displayed position and numerical value of the second thumb, and not the first thumb, in response to the user interface receiving user input (e.g., via the user input device) that selects the second thumb on the track and adjusts the position of the second thumb to increase or decrease the second range minimum without affecting the first range maximum. The method 400 returns.

By operating the slider thumbs in the unlinked mode, the output of the medical image processing system may be adjusted in real-time or near real-time based on the user input received at the user interface with increased flexibility. For example, the processor may update the displayed segmentation output on the graphical user interface as a result of an increase (or decrease) in the number of pixels of the color or fill pattern associated with one of the first range or the second range, and not the other of the first range and the second range, in response to receiving an independent adjustment of the one of the first range or second range via the corresponding slider thumb, as will be elaborated below with respect to FIG. 6.

Returning to 414, if unlinking is not requested, then the method 400 proceeds to 410 and includes maintaining the current slider control settings, as described above. As an example, the current slider settings may comprise operating in the linked mode. As such, the slider handle may be visually output via the display device of the user interface, and the value of the first range maximum and the second range minimum may be adjusted simultaneously as described herein at 420. As another example, the current slider settings may comprise the unlinking already being enabled, and the slider may continue to be operated in the unlinked mode so that the first slider thumb and the second slider thumb are adjusted independently, such as described above at 422 and 424. The method 400 returns.

Figure 5:
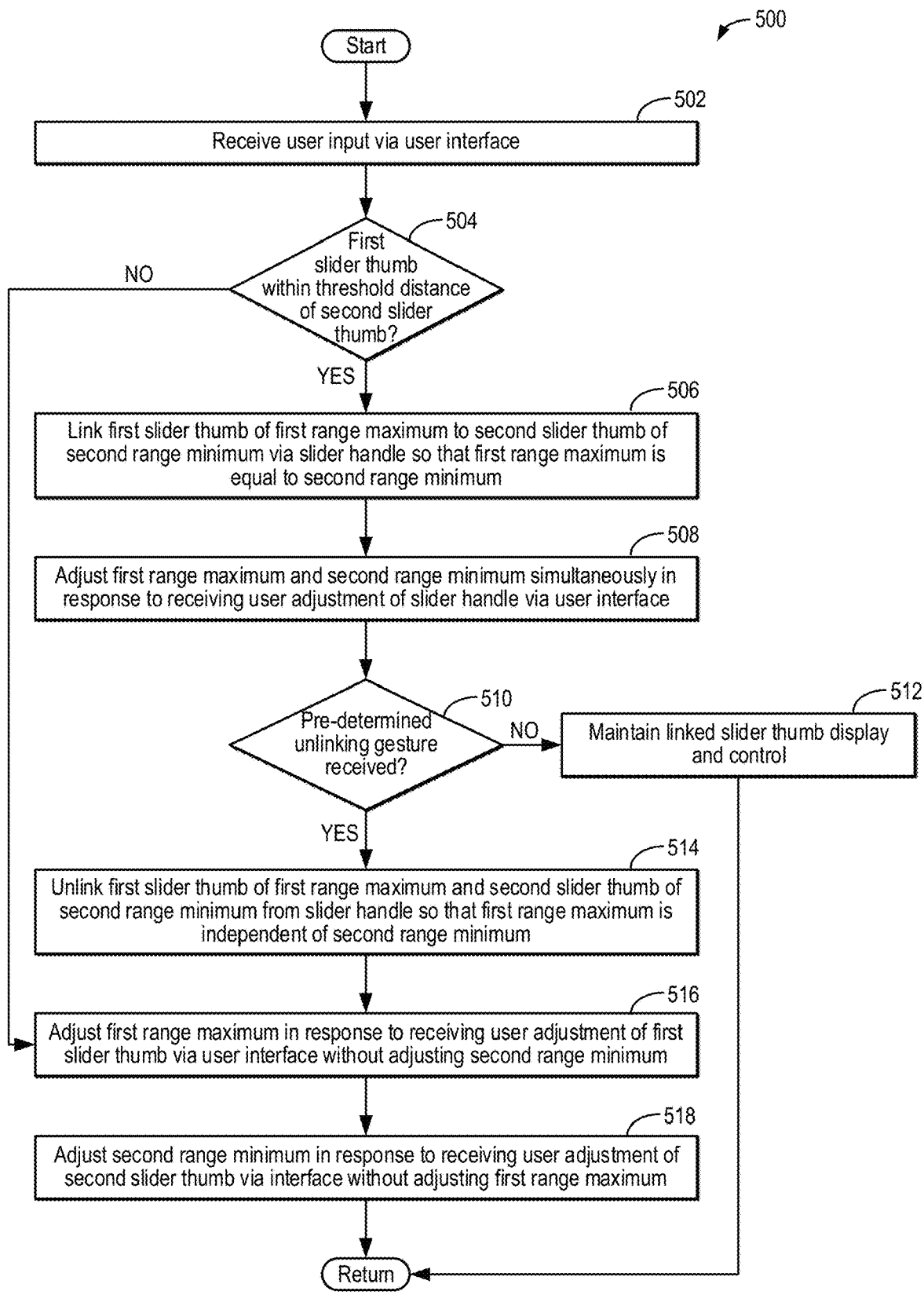
FIG. 5 is a flow chart illustrating a second example method for linking and unlinking thumbs of a slider bar.

A second example method 500 for linking and unlinking thumbs of a slider automatically via inputs received via a user interface is shown in FIG. 5. In one embodiment, the method 500 is performed by the medical image processing system 100 of FIG. 1, and the user interface may be the user interface 130 of FIG. 1. As such, the method 500 is described with respect to the system and components described above with respect to FIGS. 1-3 but may be carried with other systems/components without departing from the scope of this disclosure. As described in the method 400, the method 500 may be executed by a processor (e.g., the processor 102 of FIG. 1) according to instructions stored in non-transitory memory (e.g., the non-transitory memory 104 of FIG. 1). Although the method 500 will be described with respect to the linked and unlinked mode of a single pair of adjacent thumbs, it may be understood that the method 500 may be applied to more than one pair of adjacent thumbs. As described herein with regards to method 400, adjacent pairs of thumbs may be linked and unlinked independently from other adjacent pairs of thumbs via the method 500.

At 502, the method 500 includes receiving user input via the user interface. As one example, the user input may be acquired with a user input device, such as the user input device 134 of FIG. 1, and displayed to the user via a display device, such as the display device 132 of FIG. 1. One or both of the user input device and the display device may be operatively coupled to the user interface, such as described above with respect to FIG. 1. Additional details regarding receiving the user input via the user interface are described above at 402 of FIG. 4.

At 504, the method 500 includes determining whether a first slider thumb is within a threshold distance of a second slider thumb. As described above with respect to FIG. 4, the first slider thumb defines a first range maximum (e.g., a maximum of a first range), and the second slider thumb defines a second range minimum (e.g., a minimum of a second range that comprises larger values than the first range). The threshold distance may be calibrated to enable the automatic linking and unlinking of the first slider thumb and the second slider thumb without additional user input, such as without the slider thumb control menu input described above with respect to FIG. 4. The threshold distance may be a pre-determined, non-zero number of pixels or other measurement (e.g., a number of millimeters) that is stored in the non-transitory memory. As a non-limiting example, the threshold distance may be a value between 1 and 500 pixels. In some examples, the processor may determine that the first slider thumb is within the threshold distance from the second slider thumb in response to receiving user input (e.g., at 502) that adjusts the first slider thumb to a position on a track of the slider that is less than or equal to the threshold distance from the second slider thumb. As another example, the processor may determine that the first slider thumb is within the threshold distance from the second slider thumb in response to receiving user input that adjusts the second slider thumb to a position on the track that is less than or equal to the threshold distance from the first slider thumb. In still other examples, the processor may determine that the first slider thumb is within the threshold distance of the second slider thumb when the first slider thumb and the second slider thumb are already operating in a linked mode (e.g., the linked mode described above at 420 of FIG. 4).

If the first slider thumb is not within the threshold distance of the second slider thumb, the method 500 proceeds to 516 and includes adjusting the first range maximum in response to receiving a user adjustment of the first slider thumb via user interface without adjusting the second range minimum. Determining that the first slider thumb is not within the threshold distance of the second slider thumb may include the first slider thumb being at a position on the track that is greater than the threshold distance from the second slider thumb. As such, the processor may operate the first slider thumb and the second slider thumb in an unlinked mode and may not output a slider handle, which is used during operation in the linked mode, via the display device of the user interface. An example of operating the first slider thumb in the unlinked mode may include receiving an adjustment of the first slider thumb and updating a displayed position of the first slider thumb on the track and the corresponding numerical value of the first range maximum as the first slider thumb is being adjusted (e.g., changed) in real-time while maintaining (and not updating) a displayed position of the second slider thumb on the track and the corresponding numerical value of the second range minimum. Examples of adjusting the first range maximum in response to receiving the user adjustment of the first slider thumb via user interface without adjusting the second range minimum are described above with respect to 422 of FIG. 4.

At 518, the method 500 includes adjusting the second range minimum in response to receiving a user adjustment of the second slider thumb via user interface without adjusting the first range maximum. An example of operating the second slider thumb in the unlinked mode may include receiving an adjustment of the second slider thumb and updating (e.g., changing) the displayed position of the second slider thumb on the track and the corresponding numerical value of the second range minimum in real-time while maintaining (and not updating or changing) the displayed position of the first slider thumb and the corresponding numerical value of the first range maximum. Examples of adjusting the second range minimum in response to receiving the user adjustment of the second slider thumb via user interface without adjusting the first range maximum are described above with respect to 424 of FIG. 4. The method 500 returns.

Returning to 504, if the first slider thumb is within the threshold distance of the second slider thumb, the method 500 proceeds to 506 and includes linking the first slider thumb of the first range maximum to the second slider thumb of the second range minimum so that the first range maximum is equal to the second range minimum. As described herein, the slider handle couples the position of the first slider thumb of the first range maximum and the position of the second slider thumb of the second range minimum so that the first range maximum is equal to the second range minimum, as described above with respect to 416 of FIG. 4.

At 508, the method 500 includes adjusting the first range maximum and second range minimum simultaneously in response to receiving a user adjustment of the slider handle via the user interface. Receiving the user adjustment of the slider handle may include receiving the user adjustment at a pre-determined touch zone configured to adjust the displayed position of the first slider thumb and the second slider thumb in tandem so that the value of the second range minimum and the first range maximum share a single numerical value, as described above, and an overlapping position on the track. Examples of adjusting the first range maximum and second range minimum simultaneously in response to receiving the user adjustment of the slider handle via the user interface are described above with respect to 420 of FIG. 4.

At 510, the method 500 includes determining if a pre-determined unlinking gesture is received. The processor may enable the automatic unlinking of the first thumb and the second thumb in response to receiving the pre-determined unlinking gesture without additional user input. The pre-determined unlinking gesture may include a pre-defined interaction at a pre-determined position on the user interface that is stored in the non-transitory memory. The pre-determined position may overlap with one of the thumbs and/or the slider handle. In one example, the pre-determined position may be an unlinking touch zone of the slider handle, as described with respect to FIG. 3. In another example, the pre-determined position may be a distance of 1 mm from the unlinking touch zone. The pre-defined interaction may include a clicking action or other pre-programmed gesture at the pre-determined location. For example, the clicking action or other pre-programmed gesture may include left-clicking via a mouse, a one-fingered tap via a trackpad or touchscreen, or another type of pre-programmed user input. As an illustrative example, the pre-determined unlinking gesture may include the user selecting the unlinking touch zone of the slider handle and dragging one of the slider thumbs to be greater than the threshold distance from the other slider thumb.

If the pre-determined unlinking gesture is received, the method 500 proceeds to 514 and includes unlinking the first slider thumb of the first range maximum and the second slider thumb of the second range minimum from the slider handle so that the first range maximum is independent of the second range minimum. For example, the display device may no longer display the slider handle on the user interface in response to the processor enabling the unlinked mode. The slider handle may not be accessible by the user once the unlinked mode is enabled. The slider thumbs may then be operated in the unlinked mode, as described above at 516 and 518.

Returning to 510, if the pre-determined unlinking gesture is not received, the method 500 proceeds to 512 and includes maintaining a linked slider thumb display and control. As such, the slider handle may continue to be visually output via the display device of the user interface, and the processor may continue to operate the slider thumbs in the linked mode to adjust the first range maximum and the second range minimum simultaneously as described herein at 420 of FIG. 4. The method 500 returns. In this way, the processor may control operation of the slider thumbs and corresponding adjustments to the first range minimum and the second range maximum with reduced input from the user.

An example method 600 for adjusting medical images via a multi-range slider with linked and unlinked operating modes is shown in FIG. 6. In one embodiment, the method 600 is performed by the medical image processing system 100 of FIG. 1, and the user interface may be the user interface 130 of FIG. 1. As such, the method 600 is described with respect to the system and components described above with respect to FIGS. 1-3 but may be carried out with other systems/components without departing from the scope of this disclosure. As described in the method 400, the method 600 may be executed by a processor according to instructions stored in non-transitory memory (e.g., the processor 102 and the non-transitory memory 104 of FIG. 1). Although the method 600 will be described with respect to a single medical image, it may be understood that the method 600 may be applied to more than one medical image. For example, a first medical image may be analyzed independently from or together with a second medical image. In one embodiment, a single multi-range slider may adjust the ranges of a plurality of parameters of interest. In other embodiments, a plurality of multi-range sliders may adjust the ranges of the plurality of parameters of interest.

At 602, the method 600 includes obtaining a medical image to be analyzed. In some embodiments, the medical image may be generated by an imaging system, such as an ultrasound imaging system, a magnetic resonance imaging (MRI) system, a computed tomography (CT) system, a single-photon emission computed tomography (SPECT) system, and the like. The medical image generated by the imaging system may feature an anatomical feature of interest of a patient to aid in the diagnosis of a disease or another physical state of the patient. For example, the lungs of the patient may be featured in a chest CT image to detect and quantify different types of lesions in the lungs. In another example, the brain of a patient may be featured in a computed tomography angiography (CTA) image to differentiate cerebral vessels for ischemic stroke studies. It may be understood that the examples described above are illustrative and do not limit the scope of the disclosure. As such, the method 600 may be applied to other anatomical features and types of medical images in addition to the anatomical features and types of medical images described above.

At 604, the method 600 includes receiving initial settings for output ranges. In some examples, the initial settings may be stored in the non-transitory memory (e.g., the medical image analysis module of FIG. 1) and retrieved in response to receiving selection of the analysis to be performed on the medical image. In other examples, the initial settings may be received via user input. For example, the user may define the initial settings manually by inputting text or selecting values (e.g., from a drop-down menu) that define each of the output ranges. The output ranges may comprise a plurality of different ranges of pixel values that correspond to a feature of the medical image, such as a type of tissue or lesion. In one embodiment, the output ranges may include pixel value ranges utilized for segmenting a plurality of anatomical features in the medical image in order to differentiate the type of tissue, the type of lesion, and the like. As another example, the output ranges may comprise a plurality of different temporal ranges. For example, the temporal ranges may be used for a composite medical image generated from a time-based sequence of medical images. As a non-limiting example, the temporal ranges may be used indicate the location of a contrast dye with respect to time in the vessels of a brain of a patient. Other embodiments may use other parameter ranges to visualize the parameter of interest in the medical image displayed on the user interface to aid with medical diagnosis.

Further, each of the output ranges includes an associated visual indicator. Each visual indicator may comprise a color, a fill pattern, a line type, or the like that visually distinguishes each visual indicator from the others. For example, a first visual indicator may be calibrated to distinguish vessels, a second visual indicator may be calibrated to distinguish lesions, and a third visual indicator may be calibrated to distinguish healthy tissue. As such, the initial settings for the output ranges may define the pixel or temporal values of the medical image that are to be represented by each visual indicator in the analysis of the medical image. Further, the output ranges may be adjustable via the multi-range slider, as will be elaborated below, as each of the output ranges may comprise a range of the multi-range slider. For example, a first range of the multi-range slider may be functionally linked to the first visual indicator, a second range of the multi-range slider may be functionally linked to the second visual indicator, and so forth.

At 606, the method 600 includes determining if an output range adjustment is received. The processor may utilize user input received via a user input device to determine if an output range adjustment is received. The user input may comprise an adjustment to a position of a slider handle or a slider thumb. As described above in reference to FIGS. 2-5, each slider thumb may comprise an interactive element that defines a minimum or maximum value of one of the output ranges. Further, as described above with reference to FIGS. 3-5, the slider handle may couple the position and adjustment of two adjacent slider thumbs from two adjacent ranges (e.g., the maximum value of a first, lower range and the minimum value of a second, higher range).

If the output range adjustment is not received, the method 600 proceeds to 608 and includes analyzing the medical image using the initial settings for the output ranges. For example, processor may not receive an adjustment of any of the slider thumbs or the slider handle, when present, via the user interface. As such, the processor may use the initial settings for the output ranges in determining where to position each visual indicator on the analyzed medical image.

At 618, the method 600 includes outputting the analyzed medical image to a display. The analyzed medical image may be a transform of the medical image that includes portions (or regions) of the medical image distinguished via the visual indicators according to the pixel values or temporal data in each portion and the corresponding output range of the associated visual indicator. For example, the analyzed medical image may include a colored overlay including different colors at different tissue types. The method 600 returns.

Returning to 606, if the segmentation output range adjustment is received, the method 600 proceeds to 610 and includes determining whether the adjustment is to linked slider thumbs. As an example, receiving the output range adjustment may include receiving the selection of the slider thumb (e.g., during unlinked mode operation) or the slider handle (e.g., during linked mode operation) and positional adjustment of the slider thumb or the slider handle (e.g., to the left or to the right on the track). As such, adjustments are received for the output range(s) associated with the adjusted slider thumb or slider handle.

If the adjustment is to linked slider thumbs, the method 600 proceeds to 612 and includes adjusting adjacent slider ranges simultaneously via linked slider thumbs. Information regarding the operation settings of the multi-range slider may be stored in a user interface control module of the medical image processing system. Thus, the processor may determine whether the adjustment is made to linked slider thumbs by accessing the operation settings of the multi-range slider. Further, the slider handle may only be output for linked slider thumbs. As such, the processor may determine that the adjustment is to the linked thumbs in response to receiving, via the user interface, an adjustment of the slider handle. As described herein, the linked slider thumbs (e.g., linked via the slider handle) may adjust adjacent ranges simultaneously. For example, an adjustment to a position of the slider handle may increase the maximum value of the first range while also increasing the minimum value of the second range. Barring any adjustments to the minimum value of the first range and the maximum value of the second range, the first range may increase to encompass a larger range of values while the second range decreases to encompass a smaller range of values. Examples of adjusting linked slider thumbs to adjust medical image output ranges are described below in FIGS. 11-16, and illustrative examples of range output adjustments with linked thumbs are described below in FIGS. 7-10.

However, if it is determined at 610 that the adjustment is not linked to slider thumbs, the method 600 proceeds to 614 and includes adjusting a slider range independently from adjacent slider range(s). As one example, the processor may determine that the adjustment is made to unlinked slider thumbs by accessing the operation settings of the multi-range slider, which may indicate that the slider thumbs are operating in the unlinked mode. As another example, the processor may determine that the adjustment is not linked to slider thumbs in response to receiving the adjustment to one of the slider thumbs and not to the slider handle. As described herein, the unlinked slider thumbs may adjust the corresponding slider range independently of adjacent ranges. In one example, an adjustment to a position of an unlinked thumb of the first range may decrease the maximum value of the first range while the minimum value of the second range is unchanged. Barring any adjustments to the minimum value of the first range and the maximum value of the second range, the first range may decrease to encompass a smaller range of values while the second range remains unchanged. Examples of adjusting unlinked adjustable slider thumbs to adjust medical image output ranges is described below in FIG. 11, and illustrative examples of range output adjustments with unlinked thumbs are described below in FIGS. 7-10.

At 616, the method 600 includes analyzing the medical image using adjusted settings for the output ranges. The processor utilizes the output ranges defined by the user input received via the multi-range slider (e.g., adjustments to the ranges) to analyze the medical image and determine where to position each visual indicator on the analyzed medical image. In an example where the adjusted settings are received via linked slider thumbs, a first region (e.g., a first group of pixels) corresponding to the first range and the first visual indicator is analyzed and adjusted simultaneously with a second region (e.g., a second group of pixels) corresponding to the second range and the second visual indicator. In an example where the adjusted settings are received via unlinked slider thumbs, the first region is analyzed and adjusted independently from the second region, and vice versa.

At 618, the method 600 includes outputting the analyzed medical image to the display device, as described above. The analyzed medical image reflects the adjustments made to the output ranges via the multi-range slider in real-time or near real-time. In one example where the adjustment is received to linked slider thumbs, placement of the first visual indicator in the analyzed medical may be adjusted at the same time as the second visual indicator. For example, the size of the first region distinguished by the first visual indicator on the analyzed medical image may increase (or decrease) in real-time or near real-time at the same time that the size of the second region distinguished by the second visual indicator on the analyzed medical image decreases (or increases). In another example where the adjustment is received to an unlinked slider thumb, placement of the first visual indicator in the analyzed medical image may be adjusted on the display device in real-time or near real-time independently from the second visual indicator, and vice versa. For example, the size of the first region distinguished by the first visual indicator on the analyzed medical image may increase (or decrease) in real-time or near real-time in response to the adjustment to the first slider thumb while the size and placement of the second region may remain unchanged. The method 600 returns so that the output analyzed medical image may continue to be adjusted in real-time in response to adjustments to the output ranges received via the multi-range slider.

In reference to FIG. 7, a sequence 700 is shown that illustrates linking thumbs of two adjacent ranges of the slider 200 introduced in FIG. 2. As such, components previously introduced in FIGS. 2 and 3 are numbered the same and will not be reintroduced. The sequence 700 describes example display outputs on the user interface (e.g., displayed by the display device 132 of user interface 130 of FIG. 1) during the linking of two adjacent ranges with respect to time. Further, it may be understood that other embodiments may include alternative display outputs, numbers of adjacent ranges, and/or position adjustments of the unlinked and linked thumbs. For example, the slider 200 may be shaped as an arc instead of the linear slider shown in FIG. 7. As another example, the slider 200 may be oriented vertically instead of horizontally.

As described in FIG. 2, the slider 200 comprises the first range 214 (represented by a vertical line pattern) and the second range 216 (represented by a diamond pattern) as well as a plurality of thumbs. The first thumb 202 defines the minimum value of the first range 214, the second thumb 204 defines a maximum value of the first range 214, the third thumb 208 defines the minimum value of the second range 216, and the fourth thumb 210 defines the maximum value of the second range 216. The slider 200 further comprises the track 206 on which the first range 214 and the second range 216 may be adjusted. The track 206 comprises a fixed range of values of the slider bar. Portions of the track 206 that are not included in the first range 214 or the second range 216, referred to herein as a range gap, comprise ranges of values between the first range 214 and the second range 216 that are not included in the first range 214 or the second range 216. The slider 200 may receive input via a cursor 212, which may be controlled by a user.

A first display output 702 of the sequence 700 occurs at a time t1. In the first display output 702, the cursor 212 is not interacting with the thumbs of the slider 200, and so no adjustments are made to the first range 214 or the second range 216 or the operation of the slider thumbs. At a time t2, the slider 200 receives user input via the cursor 212 selecting the third thumb 208, as shown in a second display output 704 of the sequence 700. The user input further includes receiving, via the cursor 212, an adjustment of the third thumb 208 toward the second thumb 204, as illustrated by a third display output 706 of the sequence 700 that occurs at a time t3. As the third thumb 208 is adjusted toward the second thumb 204, the minimum value of the second range 216 decreases. Subsequently, the range gap between the first range 214 and the second range 216 is decreased, and the second range 216 is increased accordingly.

A fourth display output 708 occurs at a time t4. The fourth display output 708 illustrates a slider handle 302 introduced in FIG. 3 being output on the user interface. The slider handle 302 links the second thumb 204 and the third thumb 208 so that the thumbs are functionally coupled and share a same position on the track 206. As such, the slider handle 302 links the maximum value of the first range 214 and the minimum value of the second range 216. Further, the second thumb 204 and the third thumb 208 may be adjusted simultaneously in response to receiving user input to the slider handle 302. The linked mode of the slider 200 is enabled for the remainder of the sequence 700. Further, because the second thumb 204 is linked to the third thumb 208 via the slider handle 302, there is no longer a range gap between the first range 214 and the second range 216.

At a time t5, the user interface receives user input at a first touch zone of the slider handle 302 (e.g., the first region 310 of FIG. 3) that drags the slider handle 302 toward the fourth thumb 210, as indicated by the direction of the arrow in a fifth display output 710 of the sequence 700. In response to receiving the user input at the first touch zone of the slider handle 302, the shared position of the second thumb 204 and the third thumb 208 is adjusted toward the fourth thumb 210, as demonstrated by a sixth display output 712 at a time t6. As a result, the maximum value of the first range 214 and the minimum value of the second range 216 are both increased. Further, a span of the first range 214 is increased while a span of the second range 216 is decreased.

In reference to FIG. 8, a sequence 800 is shown that illustrates unlinking thumbs of two adjacent ranges of the slider 200. As such, components previously introduced in FIGS. 2 and 3 are numbered the same and will not be reintroduced. The sequence 800 describes display outputs of the user interface (e.g., as displayed by the display device 132 of FIG. 1) during the unlinking of two adjacent ranges with respect to time.

A first display output 802 of the sequence 800 occurs at a time t1. In the first display output 802, the second slider thumb 204 and the third slider thumb 208 are operating in the linked mode. The cursor 212 is not receiving user input, and therefore, no adjustments are made to the first range 214 or the second range 216 or the operation of the slider thumbs.

At a time t2, the user interface receives user input at a second touch zone of the slider handle 302 (e.g., the second region 312 described above in reference to FIG. 3) via the cursor 212, as shown in a second display output 804 of the sequence 800. As a result of receiving the user input at the second touch zone, the second thumb 204 and the third thumb 208 are unlinked to allow the thumbs to be adjusted independently, and the slider handle 302 is no longer output, as illustrated by a third display output 806 of the sequence 800 that occurs at a time t3.

A fourth display output 808 occurs at a time t4. The fourth display output 808 illustrates the second thumb 204 being adjusted toward the first thumb 202, as indicated by the direction of an arrow, based on user input received via the cursor 212. As a result, the maximum value of the first range 214 is decreased while the second range 216 is unchanged, as illustrated by a fifth display output 810 at a time t5. Further, the second thumb 204 continues to be adjusted toward the first thumb 202 based on the user input received via the cursor 212, widening the range gap between the first range 214 and the second range 216, as demonstrated by a sixth display output 812 output at a time t6 of the sequence 800. As a result of the adjustment in position of the second thumb 204 in the unlinked mode, the span first range 214 is decreased and while the span of the second range 216 is unchanged.

Turning now to FIG. 9, a sequence 900 is shown that illustrates linking thumbs of three adjacent ranges of a slider 901 of a user interface. The sequence 900 describes example display outputs on the user interface (e.g., as displayed by the display device 132 of FIG. 1) for the control of three adjacent ranges with respect to time. The slider 901 is similar to the slider 200 introduced in FIG. 2. As such, components previously introduced in FIGS. 2 and 3 are numbered the same and will not be reintroduced. For example, the slider 901 includes the first range 214 and the second range 216, similar to the slider 200 of FIGS. 2 and 6-7, and further includes a third range 922 (e.g., indicated by a diagonally-lined pattern). A fifth thumb 934 defines a minimum value of the third range, and a sixth thumb 936 defines a maximum value of the third range.

A first display output 902 of the sequence 900 occurs at a time t1. In the first display output 902, the cursor 212 is not interacting with the thumbs of the slider 901, and so no adjustments are made to the first range 214, the second range 216, the third range 922, or the operation of the slider thumbs. At a time t2, the slider 901 receives user input via the cursor 212 selecting the third thumb 208, as shown in a second display output 904 of the sequence 900. The user input further includes receiving, via the cursor 212, an adjustment of the third thumb 208 toward the second thumb 204, as indicated by the direction of the arrow in the second display output 904. As a result, the minimum value of the second range 214 is decreased and the range gap between the first range 214 and the second range 216 is decreased, as illustrated by a third display output 906 of the sequence 900 that occurs at a time t3.

The user input continues to adjust the third thumb 208 toward the second thumb 204, as indicated by the direction of the arrow in the third display output 906. A fourth display output 908 occurs at a time t4. The fourth display output 908 illustrates the second thumb 204 and the third thumb 208 being operated in the linked mode. The fourth display output 908 shows a first slider handle 302a functionally coupling (e.g., linking) the second thumb 204 and the third thumb 208 so that the second thumb 204 and the third thumb 208 may be adjusted simultaneously. The first slider handle 302a links the maximum value of the first range 214 and the minimum value of the second range 216. In the fourth display output 908, the first slider handle 302a is not selected via the cursor 212, and therefore, no adjustment is made to the first slider handle 302a. Instead, the user interface receives user input, via the cursor 212, selecting the fifth thumb 934 at the time t4. Further, the user input includes the fifth thumb 934 being adjusted toward the fourth thumb 210, as indicated by the direction of an arrow in the fourth display output 908. As a result of adjusting the position of the fifth thumb 934 toward the fourth thumb 210, the minimum value of the third range 922 is decreased and the range gap between the second range 216 and the third range 922 is decreased, as shown in a fifth display output 910 at a time t5 of the sequence 900.

The user input continues to adjust the fifth thumb 934 toward the fourth thumb 210, as indicated by the direction of an arrow in the fifth display output 910. A sixth display output 912 occurs at a time t6. The sixth display output 912 illustrates the fourth thumb 210 and the fifth thumb 934 being operated in the linked mode. The sixth display output 912 shows a second slider handle 302b linking the fourth thumb 210 and the fifth thumb 934 so that the fourth thumb 210 and the fifth thumb 934 may be adjusted simultaneously. The second slider handle 302b links the maximum value of the second range 216 and the minimum value of the third range 922. As such, there is no longer a range gap between the second range 216 and the third range 922.

Additionally, at the time t6, the user interface receives, via the cursor 212, user input at the first touch zone of the second slider handle 302b that adjusts the position of the second slider handle 302b toward the first slider handle 302a such that the maximum of the second range and the minimum of the third range are both decreased, as illustrated by a seventh display output 914 at a time t7.

In reference to FIG. 10, a sequence 1000 is shown that illustrates unlinking thumbs of three adjacent ranges of the slider 901 of FIG. 9. As such, components previously introduced in FIGS. 2-3 and 9 are numbered the same and will not be reintroduced. The sequence 1000 describes example display outputs on the user interface (e.g., as displayed by the display device 132 of FIG. 1) during the unlinking of three adjacent ranges with respect to time.

A first display output 1002 of the sequence 1000 occurs at a time t1. The first display output 1002 shows the slider 901 having the second thumb 204 and the third thumb 208 operating in the linked mode, as indicated by the first slider handle 302a. Further, the first display output 1002 shows the fourth thumb 210 and the fifth thumb 934 also operating in the linked mode, as indicated by the second slider handle 302b.

At a time t2, the user interface receives user input at the second touch zone (described above with reference to FIG. 3) of the slider handle 302b via the cursor 212, as shown in a second display output 1004 of the sequence 1000. In response to receiving the user input at the second touch zone, which is an unlinking touch zone, the display device no longer outputs the second slider handle 302b, as illustrated by a third display output 1006 of the sequence 1000 that occurs at a time t3, thereby unlinking the fourth thumb 210 and the fifth thumb 934 so that the fourth thumb 210 and the fifth thumb 934 may be adjusted independently.

A fourth display output 1008 occurs at a time t4. The fourth display output 1008 illustrates the cursor 212 selecting the unlinked fifth thumb 934 and adjusting the fifth thumb 934 toward the sixth thumb 936, as indicated by the direction of an arrow in the fourth display output 1008. As a result, the minimum value of the third range 922 is increased and a range gap occurs between the second range 216 and the third range 922, as illustrated by a fifth display output 1010 at a time t5. Further, the second range 216 and the first range 214 remain unchanged. Additionally, the user interface receives user input, via the cursor 212, at a second touch zone of the first slider handle 302a at the time t5. In response to receiving the user input at the second touch zone of the first slider handle 302a, the display device no longer outputs the first slider handle 302a, as illustrated by a sixth display output 1012 of the sequence 1000 that occurs at a time t6. As a result, the second thumb 202 and the third thumb 204 are operated in the unlinked mode to allow the second thumb 202 and the third thumb 204 to be adjusted independently.

At a time t7, the user interface receives user input, via the cursor 212, to select and the third thumb 208, as demonstrated by a seventh display output 1014. Further, the user input received at the time t7 adjusts the third thumb 208 toward the fourth thumb 210, as indicated by the direction of the arrow in the seventh display output 1014. As a result, the third thumb 208 is adjusted independently from the second thumb, and the second range 216 is adjusted independently from the first range 214.

FIGS. 11-13 show example display outputs of a user interface 1101. For example, each display output may be output on a display device, such as the display device 132 of FIG. 1. The user interface 1101 includes a toolbox 1104. The toolbox 1104 may include visualization tools, selection tools, segmentation tools, measuring tools, and annotation tools as some examples. The user interface 1101 further includes an image display area 1102, which shows a medical image 1106 of a lung of a patient and a segmentation output 1108 of the medical image 1106. The segmentation output 1108 shows a transformed version of the medical image 1106 with a colored overlay 1110 that visually distinguishes different portions of the segmentation output 1108 according to segmentation ranges defined in a table 1112 of the user interface 1101. In the example shown, the table 1112 includes a first column 1114, a second column 1116, a third column 1118, a fourth column 1120, and a fifth column 1122, although other numbers of columns and rows may be included in the table 1112. Further, in some embodiments, the user interface 1101 may include more than one table or may not show the table 1112.

The first column 1114 defines a range name for at least one row of the table 1112. The second column 1116 defines a plurality of ranges of image values (e.g., Hounsfield units, or HU) and the corresponding color of the colored overlay 1110 used for image portions (e.g., pixels) that fall within the given range of each row. The third column 1118 defines a percentage of pixels within the right lung that fall within the given range of each row. The fourth column 1120 defines a percentage of pixels within the left lung that fall within the given range of each row. The fifth column 1122 defines a percentage of pixels and lung volume within the combined left and right lungs that fall within the given range of each row.

The user interface 1101 further includes a multi-range slider 1124 that may be used to adjust the ranges of image values included in each segmentation range of the segmentation output 1108 and visually indicated via the colored overlay 1110. The multi-range slider 1124 includes adjustable thumbs, and pairs of adjacent adjustable thumbs may be operated in a linked mode or an unlinked mode according to the embodiments described herein.

The multi-range slider includes a first range 1128, a second range 1134 that is higher (e.g., includes greater range values) than the first range 1128, and a third range 1142 that is greater than the second range 1134. The first range 1128 corresponds to blue regions of the colored overlay 1110 and includes a first thumb 1126 defining a minimum value of the first range 1128 and a second thumb 1130 defining a maximum value of the first range 1128. The second range 1134 corresponds to green regions of the colored overlay 1110 and includes a third thumb 1132 that defines a minimum value of the second range 1134 and a fourth thumb 1136 defining a maximum value of the second range 1134. The third range 1142 corresponds to red regions of the colored overlay 1110 and includes a fifth thumb 1140 defining a minimum value of the third range 1142 and a sixth thumb 1144 defining a maximum value of the third range 1142.

The colored overlay 1110 of the segmentation output 1108 may be used to visually distinguish different tissues depicted in the medical image 1106 according to the ranges defined by the multi-range slider 1124. As a non-limiting example, the second range 1134 of the multi-range slider 1124 may represent lesions, and the third range 1142 may represent vessels. Additionally, the multi-range slider 1124 may comprise range gaps defining ranges of values that are not be included in the first range 1128, the second range 1134, or the third range 1142. In some examples, the range gaps may include image values that are anticipated to not be indicative of the tissues targeted by the image segmentation. Thus, to prevent including these data in the colored overlay 1110 of the segmentation output 1108, the values of the range gap may be adjusted in response to adjustments to the ranges of the multi-range slider 1124 (e.g., the first range 1128, the second range 1134, and the third range 1142).

It may be understood that the user interface 1101 may include more or fewer components and other configurations than that shown in FIGS. 11-13, and FIGS. 11-13 provide an illustrative example of the user interface 1101 including the multi-range slider 1124.

Referring first to FIG. 11, an example display output 1100 is shown. In the display output 1100, the second thumb 1130 and the third thumb 1132 are linked (e.g., operating in a first mode, which may be referred to as a linked mode), as indicated by a first slider handle 1138a. The first slider handle 1138a may be one embodiment of the slider handle 302 introduced in FIG. 3 and functions as previously described. In contrast, the fourth thumb 1136 and the fifth thumb 1140 are unlinked (e.g., operating in a second mode, which may be referred to as an unlinked mode). As an example, the maximum value of the first range 1128 and the minimum value of the second range 1134 may be both adjusted in response to receiving an adjustment to the first slider handle 1138a, and the segmentation output 1108 may be adjusted accordingly in real-time or near real-time to reflect the changes made to both of the first range 1128 and the second range 1134. In contrast, the maximum value of the second range 1134 and the minimum value of the third range 1142 may be adjusted individually. For example, the maximum value of the second range 1134 may be adjusted in response to input to the fourth thumb 1136 without adjusting the minimum value of the third range 1142, and the corresponding green portions shown via the colored overlay 1110 of the segmentation output 1108 may be adjusted without the red portions of the colored overlay 1110 being adjusted.

Referring next to FIG. 12, an example display output 1200 is shown. The display output 1200 shows an adjustment to the multi-range slider 1124 relative to the first display output 1100 of FIG. 11. A box 1202 highlights the ranges and corresponding color of the colored overlay 1110 that have been adjusted via the adjustment to the multi-range slider 1124 between the display output 1100 and the display output 1200. Further, the second range 1134 and the third range 1142 are operating in the linked mode, as indicated by a second slider handle 1138b surrounding the fourth thumb 1136 and the fifth thumb 1140. As shown in box 1202, the minimum value of the third range 1142 has been adjusted in response to receiving user input via the second slider handle 1138b, and as a result, the minimum value of the third range 1142 is equal to the maximum value of the second range 1134, and the range gap is no longer present.

In a comparison of the display output 1100 of FIG. 11 and the display output 1200 of FIG. 12, the first range 1128 and second 1134 range are unchanged while the third range 1142 encompasses a larger range of values due to the minimum value of the third range 1142 decreasing (e.g., due to the adjustment of the fifth thumb 1140 toward the fourth thumb 1136). Further, the third range 1142 is coupled with the second range 1134 via the second slider handle 1138b, ensuring simultaneous adjustments of the second range and third range in real-time or near real-time. In particular, the minimum value of the first range 1128 is maintained at −1024 HU and the maximum value of the first range is maintained at −487 HU while the minimum value of the second range 1134 is maintained at −487 HU and the maximum value of the second range 1134 is maintained at −268 HU. The minimum value of the third range 1142 is decreased from −30 HU to −268 HU, and the maximum value of the third range 1142 is maintained at 3071 HU, increasing the range of values included in the third range 1142 and resulting in additional red colored portions in the colored overlay 1110 of the segmentation output 1108. As described above with respect to FIG. 11, adjusting the multi-range slider 1124 results in real-time or near real-time adjustments to the segmentation output 1108 and the colored overlay 1110. For example, in response to receiving user input via the second slider handle 1138b, the minimum value of the third range 1142 is decreased and results in a greater percentage of pixels in the right lung (the third column 1118), the left lung (the fourth column 1120), and the total lung volume (the fifth column 1122) being represented by the red color in the colored overlay 1110. As such, the red (e.g., vessel) region of the colored overlay 1110 increases between the display output 1100 of FIG. 11 and the display output 1200 of FIG. 12 (e.g., an increase from 1.71% to 4.88% for the right lung).

Turning to FIG. 13, an example display output 1300 is shown. The display output 1300 shows an adjustment to the multi-range slider 1124 relative to both of the first display output 1100 of FIG. 11 and the second display output 1200 of FIG. 12. A box 1302 highlights the ranges and corresponding colors of the colored overlay 1110 that have been adjusted via the adjustment to the multi-range slider 1124 between the display output 1200 and the display output

1300. As shown in the box 1302, the minimum value of the third range 1142 has been adjusted in response to receiving user input via the second slider handle 1138b, and as a result, the minimum value of the third range 1142 is equal to the maximum value of the second range 1134, and the range gap is no longer present.

In a comparison of the display output 1200 of FIG. 12 and the display output 1300 of FIG. 13, the first range 1128 is unchanged while the second range 1134 and third range 1142 have been adjusted. For example, the second range 1134 encompasses a larger range of values due to the maximum value of the second range 1134 increasing while the third range 1142 encompasses a smaller range of values due to the minimum value of the third range 1142 increasing (e.g., due to the adjustment of the second slider handle 1138b toward the sixth thumb 1144). In particular, the minimum value of the first range 1128 is maintained at −1024 HU and the maximum value of the first range is maintained at −487 HU. With respect to the second range 1134, the minimum value of the second range 1134 is maintained at −487 HU and the maximum value of the second range 1134 is increased from −268 HU to −56 HU, thus increasing the range of values included in the second range 1134 and resulting in additional green colored portions in the colored overlay 1110 of the segmentation output 1108. The minimum value of the third range 1142 is increased from −268 HU to −56 HU, and the maximum value of the third range 1142 is maintained at 3071 HU, thus decreasing the range of values included in the third range 1142 and resulting in fewer red colored portions in the colored overlay 1110 of the segmentation output 1108.

As described above with respect to FIG. 11, adjusting the multi-range slider 1124 results in real-time or near real-time adjustments to the segmentation output 1108 and the colored overlay 1110. For example, in response to receiving user input via the second slider handle 1138b, the maximum value of the second range 1134 is increased and results in a greater percentage of pixels in the right lung (the third column 1118), the left lung (the fourth column 1120), and the total lung volume (the fifth column 1122) being represented by the green color in the colored overlay 1110. As such, the green (e.g., lesion) region of the colored overlay 1110 increases between the display output 1200 of FIG. 12 and the display output 1300 FIG. 13 (e.g., an increase from 7.5% to 10.4% for the right lung). Similarly, in response to receiving user input via the second slider handle 1138b, the minimum value of the third range 1142 is increased and results in a smaller percentage of pixels in the right lung (the third column 1118), the left lung (the fourth column 1120), and the total lung volume (the fifth column 1122) being represented by the red color in the colored overlay 1110. As such, the red (e.g., vessel) region of the colored overlay 1110 decreases between the display output 1200 of FIG. 12 and the display output 1300 of FIG. 13 (e.g., a decrease from 4.9% to 2.0% for the right lung).

FIGS. 14-16 show example display outputs of a user interface 1401. For example, each display output may be output on a display device, such as the display device 132 of FIG. 1. The user interface 1401 includes an image display area 1402, which shows an axial image output 1406 of a brain of a patient, a coronal image output 1408 of the brain of the patient, and a sagittal image output 1410 of the brain of the patient. The image outputs 1406, 1408, and 1410 each show a fusion of a plurality of contrast images obtained over a duration of a CTA scan with colored overlays 1436, 1438, and 1440 that visually distinguish different portions of the axial, coronal, and sagittal image outputs according to defined contrast uptake phases given in a key 1434, as will be elaborated below.

The user interface 1401 further includes a multi-range slider 1412 that may be used to adjust the ranges of the temporal distribution of the contrast enhancement included in each phase range of the image outputs 1406, 1408, and 1410, and visually indicated by colored overlays 1436, 1438, and 1440. The multi-range slider 1412 includes adjustable thumbs that may be operated in a linked mode or an unlinked mode according to the embodiments described herein. Values of the multi-range slider 1412 define time (e.g., in seconds) since a start of the CTA scan such that time increases (e.g., the number of seconds increases) from left to right.

The multi-range slider 1412 includes a first range 1416, a second range 1424 that is higher (e.g., includes later time values values) than the first range 1416, and a third range 1430 that is greater than the second range 1424. The first range 1416 corresponds to red regions of the colored overlays 1436, 1438, and 1440, and includes a first thumb 1414 defining a minimum value of the first range 1416 and a second thumb 1418 defining a maximum value of the first range 1416. The second range 1424 corresponds to green regions of the colored overlays 1436, 1438, and 1440, and includes a third thumb 1420 that defines a minimum value of the second range 1424 and a fourth thumb 1426 defining a maximum value of the second range 1424. The third range 1430 corresponds to blue regions of the colored overlays 1436, 1438, and 1440, and includes a fifth thumb 1428 defining a minimum value of the third range 1430 and a sixth thumb 1432 defining a maximum value of the third range 1430.

The colored overlays 1436, 1438, and 1440 of the image outputs 1406, 1408, and 1410 may be used to visually distinguish different contrast enhancement phases of cerebral vessels depicted in the medical images with respect to time, according to the temporal ranges defined by the multi-range slider 1412. As shown in the key 1434, the first range 1426 of the multi-range slider 1412 represents a pre-venous phase, the second range 1424 of the multi-range slider 1412 represents a venous phase, and the third range 1430 represents a post-venous phase.

It may be understood that the user interface 1401 may include more or fewer components and other configurations than that shown in FIGS. 14-16, and FIGS. 14-16 provide an illustrative example of the user interface 1401 including the multi-range slider 1412.

Referring first to FIG. 14, an example display output 1400 is shown. In the display output 1400, the second thumb 1418 and the third thumb 1420 are linked (e.g., operating in a first mode, which may be referred to as a linked mode), as indicated by a first slider handle 1422a. Similarly, the fourth thumb 1426 and the fifth thumb 1428 are linked, as indicated by a second slider handle 1422b. The first slider handle 1422a and the second slider handle 1422b may be one embodiment of the slider handle 302 introduced in FIG. 3 and functions as previously described. As an example, the maximum value of the first range 1416 and the minimum value of the second range 1424 may be both adjusted in response to receiving an adjustment to the first slider handle 1422a, and the colored overlays 1436, 1438, and 1440 may be adjusted accordingly in real-time or near real-time to reflect the changes made to both of the first range 1416 and the second range 1424. For example, corresponding green and red portions shown via the colored overlays 1436, 1438, and 1440 of the image outputs 1406, 1408, and 1410 may be adjusted simultaneously. As another example, the maximum value of the second range 1424 and the minimum value of the third range 1430 may be both adjusted in response to receiving an adjustment to the second slider handle 1422b, and the colored overlays 1436, 1438, and 1440 may be adjusted accordingly in real-time or near real-time to reflect the changes made to both of the second range 1424 and the third range 1430. For example, corresponding green and blue portions shown via the colored overlays 1436, 1438, and 1440 of the image outputs 1406, 1408, and 1410 may be adjusted simultaneously.

Referring next to FIG. 15, an example display output 1500 is shown. The display output 1500 shows an adjustment to the multi-range slider 1412 relative to the first display output 1400 of FIG. 14. As shown, the minimum value of the second range 1424 and the maximum value of the first range 1416 have both been adjusted toward the first thumb 1414 in response to receiving user input via the first slider handle 1422a, and as a result, the minimum value of the second range 1424 and the maximum value of the first range 1416 are decreased relative to the display output 1400 of FIG. 14. Further, the minimum value of the third range 1430 and the maximum value of the second range 1424 have both been adjusted in response to receiving user input via the second slider handle 1422b to adjust the second slider handle 1422b toward the sixth thumb 1432, and as a result, the minimum value of the third range 1430 and the maximum value of the second range 1424 are increased relative to the display output 1400 of FIG. 14.

In a comparison of the display output 1400 of FIG. 14 and the display output 1500 of FIG. 15, the first range 1416, the second 1424, and the third range 1430 are all changed. More specifically, the first range 1416 encompasses a smaller time range due to the maximum value of the first range 1416 decreasing (e.g., due to the adjustment of the second thumb 1418 toward the first thumb 1414), resulting in reduced red colored portions in the colored overlays 1436,1438, and 1440 of the image outputs 1406,1408, and 1410. In contrast, the second range 1424 encompasses a larger time range due to the minimum value of the second range 1424 decreasing and the maximum value of the second range 1424 increasing (e.g., due to the adjustment of the third thumb 1420 toward the second thumb 1418 and the adjustment of the fourth thumb 1426 toward the fifth thumb 1428). As a result, the temporal distribution of the contrast enhancement indicated by the green colored portions in the colored overlays 1436, 1438, and 1440 of the medical images increases. Further still, the third range 1430 encompasses a smaller time range due to the minimum value of the third range 1430 increasing (e.g., due to the adjustment of the fifth thumb 1428 toward the sixth thumb 1432). As such, the blue colored portions are reduced in the colored overlays 1436, 1438, and 1440 due to the smaller amount of contrast enhancement included in the smaller third range 1430.

Turning to FIG. 16, an example display output 1600 is shown. The display output 1600 shows an adjustment to the multi-range slider 1412 relative to both of the display output 1400 of FIG. 14 and the display output 1500 of FIG. 15. As shown, the minimum value of the second range 1424 and the maximum value of the first range 1416 have both been adjusted toward the fourth thumb 1426 in response to receiving user input via the first slider handle 1422a, and as a result, the minimum value of the second range 1424 and the maximum value of the first range 1416 are increased relative to the display output 1500 of FIG. 15. Further, the minimum value of the third range 1430 and the maximum value of the second range 1424 have both been adjusted in response to receiving user input via the second slider handle 1422b to adjust the second slider handle 1422b toward the sixth thumb 1432, and as a result, the minimum value of the third range 1430 and the maximum value of the second range 1424 are increased relative to the display output 1500 of FIG. 15.

In a comparison of the display output 1600 of FIG. 16 with the display output 1500 of FIG. 15, the first range 1416, the second 1424, and the third range 1430 are all changed. More specifically, the first range 1416 encompasses a larger time range due to the maximum value of the first range 1416 increasing (e.g., due to the adjustment of the second thumb 1418 toward the third thumb 1420), resulting in additional red colored portions in the colored overlays 1436, 1438, and 1440 of the image outputs 1406, 1408, and 1410. Further, the second range 1424 encompasses a smaller time range due to both of the minimum value of the second range 1424 increasing and the maximum value of the second range 1424 decreasing. As a result, the second range 1424 encompasses a smaller temporal distribution of the contrast enhancement, as illustrated by reduced green colored portions in the colored overlays 1436, 1438, and 1440 of the medical images. Further still, the third range 1430 encompasses a smaller time range due to the minimum value of the third range 1430 increasing (e.g., due to the adjustment of the fifth thumb 1428 toward the sixth thumb 1432). As such, the blue colored portions are further reduced in the colored overlays 1436, 1438, and 1440 due to the smaller amount of contrast enhancement included in the smaller third range 1430.

In this way, the multi-range slider UI component allows the user to adjust the range endpoints of adjacent ranges via UI components called thumbs. When the thumbs are linked as described herein, the user can adjust the position of both thumbs simultaneously due to the linked mode enabling dependent movement of the thumbs via the slider handle. If a user determines the medical image assessment could benefit from a more refined, manual adjustment of the ranges, then the user may disable the linked mode at the user interface, unlinking the thumbs via the slider handle and operating in an unlinked mode. Further, a processor may update values included in one or both adjacent ranges, and a resulting image analysis output, in response to receiving a single user input based on whether adjacent thumbs of the adjacent ranges are operating in the linked mode or the unlinked mode. As a result of operating the adjacent thumbs in one of the linked mode and the unlinked mode, more accurate adjustment may be made to the multi-range slider with fewer inputs and a decreased amount of time.

The technical effect of adjusting one or both of a maximum value of a first range and a minimum value of a second range that is adjacent to the first range on a slider bar in response to a single input to the slider bar based on whether operation in a linked mode or an unlinked mode is selected is that faster and more accurate control of parameters associated with each of the first range and the second range is achieved.

The disclosure also provides support for a method, comprising: displaying a slider bar comprising a track having a fixed range of values, a first slider thumb defining a maximum value of a first adjustable range on the track, and a second slider thumb defining a minimum value of a second adjustable range on the track, operating the first slider thumb and the second slider thumb in one of a linked mode and an unlinked mode, and adjusting one or both of the maximum value of the first adjustable range and the minimum value of the second adjustable range in response to receiving a single user input based on whether the first slider thumb and the second slider thumb are operating in the linked mode or the unlinked mode. In a first example of the method, the method further comprises: setting the maximum value of the first adjustable range to be equal to the minimum value of the second adjustable range in response to operating the first slider thumb and the second slider thumb in the linked mode, displaying the first slider thumb and the second slider thumb at a same position on the track in response to operating the first slider thumb and the second slider thumb in the linked mode, and displaying a slider handle configured to adjust both of the first slider thumb and the second slider thumb simultaneously in response to operating the first slider thumb and the second slider thumb in the linked mode. In a second example of the method, optionally including the first example, adjusting one or both of the maximum value of the first adjustable range and the minimum value of the second adjustable range in response to receiving the single user input based on whether the first slider thumb and the second slider thumb are operating in the linked mode or the unlinked mode comprises: operating the first slider thumb and the second slider thumb in the linked mode at a first time, adjusting both of the maximum value of the first adjustable range and the minimum value of the second adjustable range in response to receiving the single user input at the first time, operating the first slider thumb and the second slider thumb in the unlinked mode at a second time, and adjusting one of, and not the other of, the maximum value of the first adjustable range and the minimum value of the second adjustable range in response to receiving the single user input at the second time. In a third example of the method, optionally including one or both of the first and second examples, receiving the single user input at the first time comprises receiving an adjustment of a position of the slider handle on the track. In a fourth example of the method, optionally including one or more or each of the first through third examples, receiving the single user input at the second time comprises receiving an adjustment of a position of one of, and not the other of, the first slider thumb and the second slider thumb on the track. In a fifth example of the method, optionally including one or more or each of the first through fourth examples, the method further comprises: transitioning from operating the first slider thumb and the second slider thumb in the unlinked mode to operating the first slider thumb and the second slider thumb in the linked mode in response to receiving a first pre-determined input while operating the first slider thumb and the second slider thumb in the unlinked mode, transitioning from operating the first slider thumb and the second slider thumb in the linked mode to operating the first slider thumb and the second slider thumb in the unlinked mode in response to receiving a second pre-determined input while operating the first slider thumb and the second slider thumb in the linked mode, and removing the slider handle in response to transitioning from the linked mode to the unlinked mode in response. In a sixth example of the method, optionally including one or more or each of the first through fifth examples, receiving the first pre-determined input comprises a linked mode option of a slider thumb control menu being selected via a user interface, and wherein receiving the second pre-determined input comprises an unlinked mode option of the slider thumb control menu being selected via the user interface. In a seventh example of the method, optionally including one or more or each of the first through sixth examples, receiving the first pre-determined input comprises receiving, via a user interface, an adjustment of one of the first slider thumb and the second slider thumb that brings the first slider thumb within a threshold distance of the second slider thumb on the track, and wherein receiving the second pre-determined input comprises receiving a pre-determined unlinking gesture at an unlinking touch zone of the slider handle via the user interface. In an eighth example of the method, optionally including one or more or each of the first through seventh examples, the second adjustable range is adjacent to the first adjustable range and comprises larger values of the fixed range of values than the first adjustable range, and the method further comprises: displaying an overlay on a medical image, the overlay including a first visual indicator at pixels of the medical image having values within the first adjustable range and a second visual indicator at pixels of the medical image having values within the second adjustable range, and adjusting the overlay in response to receiving the single user input, including adjusting one or both of the first visual indicator and the second visual indicator in response to receiving the single user input based on whether the first slider thumb and the second slider thumb are operating in the linked mode or the unlinked mode. In a ninth example of the method, optionally including one or more or each of the first through eighth examples, adjusting one or both of the first visual indicator and the second visual indicator in response to receiving the single user input based on whether the first slider thumb and the second slider thumb are operating in the linked mode or the unlinked mode comprises: adjusting both of the first visual indicator and the second visual indicator in response to receiving the single user input while operating the first slider thumb and the second slider thumb in the linked mode, and adjusting one of, and not the other of, the first visual indicator and the second visual indicator in response to receiving the single user input while operating the first slider thumb and the second slider thumb in the unlinked mode.

The disclosure also provides support for a method, comprising: displaying, via a user interface, an analysis output of a medical image comprising a first visual indicator at a first group of pixels of the medical image having values within a first adjustable range and a second visual indicator at a second group of pixels of the medical image having values within a second adjustable range, displaying, via the user interface, a slider bar comprising the first adjustable range and the second adjustable range on a track having a fixed range of values, operating the slider bar in a first mode at a first time, simultaneously adjusting both of the first visual indicator and the second visual indicator in response to receiving, via the user interface, a first adjustment to the slider bar while operating in the first mode, operating the slider bar in a second mode at a second time, and adjusting one of the first visual indicator and the second visual indicator in response to receiving, via the user interface, a second adjustment to the slider bar while operating in the second mode. In a first example of the method, the slider bar further comprises a first adjustable thumb defining a maximum value of the first adjustable range and a second adjustable thumb defining a minimum value of the second adjustable range, and wherein operating the slider bar in the first mode at the first time comprises: displaying, via the user interface, a slider handle that is configured to operatively couple and simultaneously adjust the first adjustable thumb and the second adjustable thumb, setting the maximum value of the first adjustable range to be equal to the minimum value of the second adjustable range, and simultaneously adjusting both of the maximum value of the first adjustable range and the minimum value of the second adjustable range in response to receiving, via the user interface, the first adjustment to the slider bar via the slider handle. In a second example of the method, optionally including the first example, operating the slider bar in the second mode at the second time comprises: not displaying the slider handle via the user interface, adjusting the maximum value of the first adjustable range, and not the minimum value of the second adjustable range, in response to response to receiving, via the user interface, the second adjustment to the slider bar via the first adjustable thumb, and adjusting the minimum value of the second adjustable range, and not the maximum value of the first adjustable range, in response to receiving, via the user interface, the second adjustment to the slider bar via the second adjustable thumb. In a third example of the method, optionally including one or both of the first and second examples, simultaneously adjusting both of the first visual indicator and the second visual indicator in response to receiving, via the user interface, the first adjustment to the slider bar while operating in the first mode comprises: simultaneously adjusting pixels of the medical image included in both of the first group of pixels and the second group of pixels in real-time responsive to receiving the first adjustment to the slider bar, and updating the analysis output displayed via the user interface based on the adjusted first group of pixels and the adjusted second group of pixels in real-time. In a fourth example of the method, optionally including one or more or each of the first through third examples, adjusting one of the first visual indicator and the second visual indicator in response to receiving, via the user interface, the second adjustment to the slider bar while operating in the second mode comprises: adjusting pixels of the medical image included in one of, and not the other of, the first group of pixels and the second group of pixels in real-time responsive to receiving the second adjustment to the slider bar, and updating the analysis output displayed via the user interface based on the adjusted one of the first group of pixels and the second group of pixels in real-time.

The disclosure also provides support for a system, comprising: a user interface, and a processor operatively coupled to the user interface and executable instructions stored in non-transitory memory that, when executed, cause the processor to: display, via the user interface, a slider bar comprising a first slider thumb defining a maximum value of a first adjustable range on a track and a second slider thumb defining a minimum value of a second adjustable range on the track, the second adjustable range adjacent to the first adjustable range on the track and comprising larger values than the first adjustable range, operate the first slider thumb and the second slider thumb in a linked mode in response to receiving a pre-determined linking input via the user interface, display, via the user interface, a slider handle surrounding the first slider thumb and the second slider thumb while operating in the linked mode, the slider handle comprising a first touch zone configured to receive input via the user interface and simultaneously adjust the maximum value of the first adjustable range and the minimum value of the second adjustable range in response to the input, and operate the first slider thumb and the second slider thumb in an unlinked mode in response to receiving a pre-determined unlinking input via the user interface. In a first example of the system, receiving the pre-determined linking input via the user interface comprises receiving a selection of the linked mode in a slider thumb control menu displayed via the user interface, and wherein receiving the pre-determined unlinking input via the user interface comprises receiving the selection of the unlinked mode in the slider thumb control menu. In a second example of the system, optionally including the first example, receiving the pre-determined linking input via the user interface comprises receiving, via the user interface, an adjustment of one of the first slider thumb and the second slider thumb that brings the first slider thumb within a threshold distance of the second slider thumb on the track, and wherein receiving the pre-determined unlinking input via the user interface comprises receiving, via the user interface, input at a second touch zone of the slider handle configured to unlink the first slider thumb and the second slider thumb and hide the slider handle. In a third example of the system, optionally including one or both of the first and second examples, the processor executes further instructions stored in the non-transitory memory that cause the processor to: not display the slider handle while operating in the unlinked mode, adjust the maximum value of the first adjustable range without adjusting the minimum value of the second adjustable range in response to receiving, via the user interface, an adjustment to the first slider thumb while operating the first slider thumb and the second slider thumb in the unlinked mode, and adjust the minimum value of the second adjustable range without adjusting the maximum value of the first adjustable range in response to receiving, via the user interface, the adjustment to the second slider thumb while operating the first slider thumb and the second slider thumb in the unlinked mode. In a fourth example of the system, optionally including one or more or each of the first through third examples, the processor executes further instructions stored in the non-transitory memory that cause the processor to: display, via the user interface, an overlay on a medical image, the overlay including a first color at pixels of the medical image having values within the first adjustable range and a second color at pixels of the medical image having values within the second adjustable range, adjust pixels depicted by both of the first color and the second color in response to receiving, via the user interface, the input at the first touch zone of the slider handle while operating in the linked mode, adjust pixels depicted by the first color, and not the second color, in response to receiving, via the user interface, an adjustment to the first slider thumb while operating the first slider thumb and the second slider thumb in the unlinked mode, and adjust pixels depicted by the second color, and not the first color, in response to receiving, via the user interface, the adjustment to the second slider thumb while operating the first slider thumb and the second slider thumb in the unlinked mode.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
displaying a slider bar comprising a track having a fixed range of values, a first slider thumb defining a maximum value of a first adjustable range on the track, and a second slider thumb defining a minimum value of a second adjustable range on the track;
operating the first slider thumb and the second slider thumb in one of a linked mode and an unlinked mode;
adjusting one or both of the maximum value of the first adjustable range and the minimum value of the second adjustable range in response to receiving a single user input based on whether the first slider thumb and the second slider thumb are operating in the linked mode or the unlinked mode;
setting the maximum value of the first adjustable range to be equal to the minimum value of the second adjustable range in response to operating the first slider thumb and the second slider thumb in the linked mode;
displaying the first slider thumb and the second slider thumb at a same position on the track in response to operating the first slider thumb and the second slider thumb in the linked mode; and
displaying a slider handle configured to adjust both of the first slider thumb and the second slider thumb simultaneously in response to a single user input operating the first slider thumb and the second slider thumb in the linked mode.

2. The method of claim 1, wherein adjusting one or both of the maximum value of the first adjustable range and the minimum value of the second adjustable range in response to receiving the single user input based on whether the first slider thumb and the second slider thumb are operating in the linked mode or the unlinked mode comprises:
operating the first slider thumb and the second slider thumb in the linked mode at a first time;
adjusting both of the maximum value of the first adjustable range and the minimum value of the second adjustable range in response to receiving the single user input at the first time;
operating the first slider thumb and the second slider thumb in the unlinked mode at a second time; and
adjusting one of, and not the other of, the maximum value of the first adjustable range and the minimum value of the second adjustable range in response to receiving the single user input at the second time.

3. The method of claim 2, wherein receiving the single user input at the first time comprises receiving an adjustment of a position of the slider handle on the track.

4. The method of claim 2, wherein receiving the single user input at the second time comprises receiving an adjustment of a position of one of, and not the other of, the first slider thumb and the second slider thumb on the track.

5. The method of claim 1, further comprising:
transitioning from operating the first slider thumb and the second slider thumb in the unlinked mode to operating the first slider thumb and the second slider thumb in the linked mode in response to receiving a first pre-determined input while operating the first slider thumb and the second slider thumb in the unlinked mode;
transitioning from operating the first slider thumb and the second slider thumb in the linked mode to operating the first slider thumb and the second slider thumb in the unlinked mode in response to receiving a second pre-determined input while operating the first slider thumb and the second slider thumb in the linked mode; and
removing the slider handle in response to transitioning from the linked mode to the unlinked mode in response.

6. The method of claim 5, wherein receiving the first pre-determined input comprises a linked mode option of a slider thumb control menu being selected via a user interface, and wherein receiving the second pre-determined input comprises an unlinked mode option of the slider thumb control menu being selected via the user interface.

7. The method of claim 5, wherein receiving the first pre-determined input comprises receiving, via a user interface, an adjustment of one of the first slider thumb and the second slider thumb that brings the first slider thumb within a threshold distance of the second slider thumb on the track, and wherein receiving the second pre-determined input comprises receiving a pre-determined unlinking gesture at an unlinking touch zone of the slider handle via the user interface.

8. The method of claim 1, wherein the second adjustable range is adjacent to the first adjustable range and comprises larger values of the fixed range of values than the first adjustable range, and the method further comprises:
displaying an overlay on a medical image, the overlay including a first visual indicator at pixels of the medical image having values within the first adjustable range and a second visual indicator at pixels of the medical image having values within the second adjustable range; and
adjusting the overlay in response receiving the single user input, including adjusting one or both of the first visual indicator and the second visual indicator in response to receiving the single user input based on whether the first slider thumb and the second slider thumb are operating in the linked mode or the unlinked mode.

9. The method of claim 8, wherein adjusting one or both of the first visual indicator and the second visual indicator in response to receiving the single user input based on whether the first slider thumb and the second slider thumb are operating in the linked mode or the unlinked mode comprises:
adjusting both of the first visual indicator and the second visual indicator in response to receiving the single user input while operating the first slider thumb and the second slider thumb in the linked mode; and
adjusting one of, and not the other of, the first visual indicator and the second visual indicator in response to receiving the single user input while operating the first slider thumb and the second slider thumb in the unlinked mode.

10. A method, comprising:
displaying, via a user interface, an analysis output of a medical image comprising a first visual indicator at a first group of pixels of the medical image having values within a first adjustable range and a second visual indicator at a second group of pixels of the medical image having values within a second adjustable range;
displaying, via the user interface, a slider bar comprising the first adjustable range and the second adjustable range on a track having a fixed range of values;
operating the slider bar in a first mode at a first time;
simultaneously adjusting both of the first visual indicator and the second visual indicator in response to receiving, via the user interface, a first adjustment to the slider bar while operating in the first mode;

operating the slider bar in a second mode at a second time; and adjusting one of the first visual indicator and the second visual indicator in response to receiving, via the user interface, a second adjustment to the slider bar while operating in the second mode;

wherein the slider bar further comprises a first adjustable thumb defining a maximum value of the first adjustable range and a second adjustable thumb defining a minimum value of the second adjustable range, and wherein operating the slider bar in the first mode at the first time comprises:

displaying, via the user interface, a slider handle that is configured to operatively couple and simultaneously adjust the first adjustable thumb and the second adjustable thumb;

setting the maximum value of the first adjustable range to be equal to the minimum value of the second adjustable range; and simultaneously adjusting both of the maximum value of the first adjustable range and the minimum value of the second adjustable range in response to receiving, via the user interface, the single first adjustment to the slider bar via the slider handle.

11. The method of claim 10, wherein operating the slider bar in the second mode at the second time comprises:

not displaying the slider handle via the user interface;

adjusting the maximum value of the first adjustable range, and not the minimum value of the second adjustable range, in response to response to receiving, via the user interface, the second adjustment to the slider bar via the first adjustable thumb; and adjusting the minimum value of the second adjustable range, and not the maximum value of the first adjustable range, in response to receiving, via the user interface, the second adjustment to the slider bar via the second adjustable thumb.

12. The method of claim 10, wherein simultaneously adjusting both of the first visual indicator and the second visual indicator in response to receiving, via the user interface, the first adjustment to the slider bar while operating in the first mode comprises:

simultaneously adjusting pixels of the medical image included in both of the first group of pixels and the second group of pixels in real-time responsive to receiving the first adjustment to the slider bar; and updating the analysis output displayed via the user interface based on the adjusted first group of pixels and the adjusted second group of pixels in real-time.

13. The method of claim 10, wherein adjusting one of the first visual indicator and the second visual indicator in response to receiving, via the user interface, the second adjustment to the slider bar while operating in the second mode comprises:

adjusting pixels of the medical image included in one of, and not the other of, the first group of pixels and the second group of pixels in real-time responsive to receiving the second adjustment to the slider bar; and updating the analysis output displayed via the user interface based on the adjusted one of the first group of pixels and the second group of pixels in real-time.

14. A system, comprising:
a user interface; and
a processor operatively coupled to the user interface and executable instructions stored in non-transitory memory that, when executed, cause the processor to:

display, via the user interface, a slider bar comprising a first slider thumb defining a maximum value of a first adjustable range on a track and a second slider thumb defining a minimum value of a second adjustable range on the track, the second adjustable range adjacent to the first adjustable range on the track and comprising larger values than the first adjustable range;

operate the first slider thumb and the second slider thumb in a linked mode in response to receiving a pre-determined linking input via the user interface;

display, via the user interface, a slider handle surrounding the first slider thumb and the second slider thumb while operating in the linked mode, the slider handle comprising a first touch zone configured to receive input via the user interface and simultaneously adjust the maximum value of the first adjustable range and the minimum value of the second adjustable range in response to the input, the maximum value of the first adjustable range being the same as the minimum value of the second adjustable range; and operate the first slider thumb and the second slider thumb in an unlinked mode in response to receiving a pre-determined unlinking input via the user interface.

15. The system of claim 14, wherein receiving the pre-determined linking input via the user interface comprises receiving a selection of the linked mode in a slider thumb control menu displayed via the user interface, and wherein receiving the pre-determined unlinking input via the user interface comprises receiving the selection of the unlinked mode in the slider thumb control menu.

16. The system of claim 14, wherein receiving the pre-determined linking input via the user interface comprises receiving, via the user interface, an adjustment of one of the first slider thumb and the second slider thumb that brings the first slider thumb within a threshold distance of the second slider thumb on the track, and wherein receiving the pre-determined unlinking input via the user interface comprises receiving, via the user interface, input at a second touch zone of the slider handle configured to unlink the first slider thumb and the second slider thumb and hide the slider handle.

17. The system of claim 14, wherein the processor executes further instructions stored in the non-transitory memory that cause the processor to:

not display the slider handle while operating in the unlinked mode;

adjust the maximum value of the first adjustable range without adjusting the minimum value of the second adjustable range in response to receiving, via the user interface, an adjustment to the first slider thumb while operating the first slider thumb and the second slider thumb in the unlinked mode; and adjust the minimum value of the second adjustable range without adjusting the maximum value of the first adjustable range in response to receiving, via the user interface, the adjustment to the second slider thumb while operating the first slider thumb and the second slider thumb in the unlinked mode.

18. The system of claim 14, wherein the processor executes further instructions stored in the non-transitory memory that cause the processor to:
- display, via the user interface, an overlay on a medical image, the overlay including a first color at pixels of the medical image having values within the first adjustable range and a second color at pixels of the medical image having values within the second adjustable range;
- adjust pixels depicted by both of the first color and the second color in response to receiving, via the user interface, the input at the first touch zone of the slider handle while operating in the linked mode;
- adjust pixels depicted by the first color, and not the second color, in response to receiving, via the user interface, an adjustment to the first slider thumb while operating the first slider thumb and the second slider thumb in the unlinked mode; and
- adjust pixels depicted by the second color, and not the first color, in response to receiving, via the user interface, the adjustment to the second slider thumb while operating the first slider thumb and the second slider thumb in the unlinked mode.

19. The method of claim 1, wherein, when in linked mode, the first adjustable range and the second adjustable range only overlap at the value that is the maximum of the first adjustable range and the minimum of the second adjustable range.

20. The method of claim 19, wherein, when in linked mode, adjustments by user control do not adjust the overlap between the first adjustable range and the second adjustable range.

* * * * *